(12) United States Patent
Kieny

(10) Patent No.: US 6,261,799 B1
(45) Date of Patent: Jul. 17, 2001

(54) EXPRESSION CASSETTES ENCODING SOLUBLE, NON-CLEAVABLE, CHIMERIC HIV-1 GP160 VARIANTS, THEIR METHODS OF CONSTRUCTION, AND METHODS FOR THE PRODUCTION OF GP160 VARIANTS

(75) Inventor: Marie-Paule Kieny, Strasbourg (FR)

(73) Assignee: Transgene S.A., Strasbourg (FR)

( * ) Notice: Subject to any disclaimer, the term of this patent is extended or adjusted under 35 U.S.C. 154(b) by 0 days.

(21) Appl. No.: 07/956,483

(22) PCT Filed: Apr. 30, 1992

(86) PCT No.: PCT/FR92/00394

§ 371 Date: Dec. 31, 1992

§ 102(e) Date: Dec. 31, 1992

(87) PCT Pub. No.: WO92/19742

PCT Pub. Date: Nov. 12, 1992

(30) Foreign Application Priority Data

May 2, 1991 (FR) .................................... 91 05392

(51) Int. Cl.[7] .................................... C12P 21/05
(52) U.S. Cl. ............... 435/69.1; 424/188.1; 424/208.1; 424/93.2
(58) Field of Search ................ 435/69.1, 69.3, 435/70.1, 71.1, 172.3; 530/380; 536/23.22; 424/188.1

(56) References Cited

U.S. PATENT DOCUMENTS 5,169,763 * 12/1992 Kieny et al. ...................... 435/69.3

FOREIGN PATENT DOCUMENTS 0 272 858 * of 1988 (EP) .................. C12N/15/00
0 335 635 * of 1989 (EP) .................. C12N/15/00

OTHER PUBLICATIONS

AIDS Research and Human Retroviruses, "Safety and Immunogenicity of a Recombinant HIV Type 1 Glycoprotein 160 Boosted by a V3 Synthetic Peptide in HIV-Negative Volunteers", vol. 11, Nov. 12, 1995, Mary Anne Liebert, Inc.*

Pantaleo et al., 1993, "The immunopathogenesis of human immunodeficiency virus infection", New Engl. J. Med. 328:327–335.*

Tindall and Cooper, 1991, "Primary HIV infection: host responses and intervention strategies", AIDS 5:1–14.*

Letvin, N., 1993, "Vaccines against human immunodeficiency virus: progress and prospects", New Engl. J. Med. 329:1400–1405.*

Haynes, B., 1993, "Scientific and social issues of human immunodeficiency virus vaccine development", 260:1279–1286.*

Kellogg and Kwok, 1990, "Detection of human immunodeficiency virus", in PCR Protocols: A Guide to Methods and Applications, Academic Press, pp. 337–347.*

* cited by examiner

Primary Examiner—Laurie Scheiner
Assistant Examiner—Jeffrey S. Parkin
(74) Attorney, Agent, or Firm—Burns, Doane, Swecker & Mathis, L.L.P.

(57) ABSTRACT

This invention is directed toward soluble, non-cleavable, chimeric human immunodeficiency virus type 1 (HIV-1) gp160 variants, expression vectors encoding said variants, and methods of producing said variants. These HIV-1 gp160 variants comprise the following regions: I) a first region derived from the gp160 of a first strain of HIV-1; ii) a second region derived from the gp160 of a second strain of HIV-1 wherein said second region fails to contain functional major and minor proteolytic cleavage sites (amino acids 483–486 and 475–479, respectively) and functional major and minor hydrophobic domains (amino acids 487–516 and 659–680, respectively); and iii) an optional third region, derived from the gp160 of said second strain, located at the amino terminus of the recombinant envelope.

44 Claims, No Drawings

EXPRESSION CASSETTES ENCODING SOLUBLE, NON-CLEAVABLE, CHIMERIC HIV-1 GP160 VARIANTS, THEIR METHODS OF CONSTRUCTION, AND METHODS FOR THE PRODUCTION OF GP160 VARIANTS

The present invention relates to a method for constructing means needed for the production of new molecules capable of inducing an immunoprotective response against a virus responsible for acquired immunodeficiency syndrome (AIDS).

In an individual, this disease develops following an infection of T-helper lymphocytes by an HIV (human immunodeficiency virus) retrovirus. To date, these retroviruses have been classified in two major types: type HIV-1, which is rife essentially in Europe and North America, and type HIV-2, which is characteristic of African infections. Within a given type, the HIV retro-viruses exhibit some degree of variability from one another, which is characterized, for example, by a difference in cellular trophism or by viral proteins that differ slightly from one another. For this reason, when it is desired to refer to a particular HIV retrovirus, the term "viral strain" is preferably employed.

Generally speaking, HIV retroviruses have the following structure: the genomic RNA molecule and various associated proteins are encapsulated in a capsid of protein nature (nucleocapsid). The whole is protected by a membrane of cellular origin which has incorporated the envelope protein of viral origin.

This envelope protein, in various forms, is considered at the present time to be a potential therapeutic component of a vaccine against AIDS.

Under natural conditions, the envelope protein (env) is initially synthesized in the form of a precursor, containing at its N-terminal end a signal sequence which initiates the passage of the precursor into the endoplasmic reticulum (secretion route). This signal peptide is then removed by proteolytic cleavage. The product of this cleavage is a protein referred to as gp160, which is itself subsequently cleaved into a gp40 small subunit and a gp120 large subunit. The N-terminal end of the gp120 corresponds to the N-terminal end of the gp160, while the C-terminal end of the gp40 corresponds to the C-terminal end of the gp160.

Each of these subunits is secreted out of the infected cell. However, the gp40 remains anchored in the cell membrane via its transmembrane domain. Its C-terminal portion (intracytoplasmic domain) remains in contact with the cytoplasm, while its N-terminal portion (extracytoplasmic domain) is at the cell surface. The gp120 subunit is released outside the cell, where it interacts with the extracellular domain of the gp40 subunit. The two subunits of the envelope protein thus remain associated in the form of a complex.

The amino acid sequence of the precursors of the env proteins of various viral strains are now known. As an example, FIG. 1 presents the sequence of the precursors of the gp160 proteins of the viral strains HIV-1 Bru, HIV-1 MN, HIV-1 ELI, HIV-1 RF, HIV-1 SF2C and HIV-1 SC. Similarly, FIG. 2 presents the sequence of the precursor of the gp160 of the viral strain HIV-2 Rod.

Hereinafter, and to make the text easier to understand, the sequences of the gp160 proteins other than the gp160 of the strain HIV-1 Bru will be described below by reference to the sequence of the gp160 of the strain HIV-1 Bru (hereinafter referred to as gp160-Bru) as follows:

a) gp160-Bru possesses 831 amino acids, these being numbered from 1 to 831. In addition, gp120-Bru corresponds to the sequence of the first 486 amino acids of gp160-Bru, while gp40-Bru corresponds to the sequence beginning with the amino acid at position 487 and ending with the amino acid at position 831.

b) The sequence of a gp160 of any kind is aligned with the sequence of gp160-Bru so as to display maximum homology. For this purpose, gaps may be introduced either into the sequence of gp160-Bru or into the sequence of the gp160 of any kind. By definition, the position of an amino acid in the gp160 of any kind will be specified in identical fashion by the position of the homologous amino acid in gp160-Bru.

c) Consequently, when a gap is introduced into the sequence of the gp160 of any kind, opposite the amino acid at position x, there is no amino acid at position x in the sequence of the gp160. However, this amino acid is considered to possess a virtual presence.

d) When one or more gap(s) is/are introduced into the sequence of gp160-Bru between the amino acid at position x and the amino acid at position x+1, it is considered that, in the gp160 of any kind, the position covers at least two subpositions $x_a$, $x_b$, . . . , $x_n$, each occupied by an amino acid. By definition, the downstream position $x_n$ represents the position x.

e) When one or more gap(s) is/are introduced into the sequence of gp160-Bru upstream of the amino acid at position 1, it is considered that, in the gp160 of any kind, the position 1 covers at least two subpositions $1_a$, $1_b$, . . . , $1_n$, each occupied by an amino acid. By definition, the $NH_2$-terminal upstream position $1_n$ represents the position 1.

f) When one or more gap(s) is/are introduced into the sequence of the gp160 of any kind opposite the $NH_2$-terminal amino acid(s) of gp160-Bru, it may be noted that, by definition, the amino acid at the $NH_2$-terminal position in the gp160 of any kind holds simultaneously the position 1 and its position of homologous amino acid.

g) When one or more gap(s) is/are introduced into the sequence of the gp160 of any kind opposite the COOH-terminal amino acid(s) of gp160-Bru, it may be noted that, by definition, the amino acid at the COOH-terminal position in the gp160 of any kind holds simultaneously the position 841 and its position of homologous amino acid.

At the present time, with regard to a vaccine, envelope protein is considered to be a potentially advantageous candidate from a therapeutic standpoint. However, its multi-chain structure in the original state constitutes a handicap in terms of feasibility. For this reason, it has been seen to be preferable to use a single-chain protein which would retain most of the epitopes of the gp120 and those of the gp40. This type of protein has already been proposed in Patent Application WO 87/6260. It is, more especially, a non-cleavable and soluble gp160 variant.

All the gp160 proteins of type HIV-1 viral strains possess, at positions 483–486, a so-called major cleavage site, recognized by one or more proteolytic enzymes. This cleavage site is the same for all the gp160 proteins described in FIG. 1, and corresponds to the sequence [SEQ ID NO.:1] Arg-Glu-Lys-Arg (REKR). The proteolytic enzymes cut immediately downstream of this cleavage site to release a gp120 and a gp40.

When this cleavage site is not there, it has been demonstrated that the proteolytic enzymes recognize, albeit with lower efficiency, a so-called minor cleavage site, and to make [sic] a cut immediately downstream of the latter. Here too, this cleavage site is the same for all the gp160 proteins shown in FIG. 1. It corresponds to the sequence Lys-Arg-Arg (KRR) at positions 477–479, according to some authors or, according to others, the sequence [SEQ ID NO.:2] Lys-Ala-Lys-Arg (KAKR) at positions 475–478.

In addition, it may be noted that the gp160 proteins of type HIV-2 viral strains possess only a major cleavage site at positions 475–478, which corresponds to the sequence [SEQ ID NO.:3] Lys-Glu-Lys-Arg (KEKR).

A non-cleavable gp160 variant is an artificial analog of a native gp160. Its amino acid sequence corresponds to that of a native gp160 in which the major cleavage site and/or the minor cleavage site has/have been eliminated.

Such a gp160 variant may be synthesized by means of recombinant DNA techniques. It suffices to isolate a DNA fragment coding for a native gp160, and then to modify the region coding for the major cleavage site by directed mutagenesis so as to obtain a DNA fragment coding for a gp160 variant insensitive to proteolytic action. This latter DNA fragment is subsequently expressed under suitable conditions to give said gp160 variant. Such a gp160 variant which no longer contains the major cleavage site is referred to hereinafter as a type A non-cleavable gp160 variant.

Preferably, the region coding for the minor cleavage site can be, in addition, modified for identical purposes. Under these conditions, a type A' non-cleavable gp160 variant, which contains neither the major cleavage site nor the minor cleavage site, is obtained.

For this purpose, it may be noted, as an example, that the cleavage site REKR, KEKR or KAKR and the cleavage site KRR may be replaced, respectively, by the sequences [SEQ ID NO.:4] Asn-Glu-His-Gln (NEHQ) and Gln-Asn-His (QNH).

Moreover, it is also necessary for a gp160 to be obtained in soluble form. Such a gp160 corresponds to a native gp160 in which the transmembrane region of hydrophobic nature has been eliminated. This transmembrane region is located in the zone corresponding to the gp40, from the amino acid residue at position 659 to the amino acid residue at position 680. Additionally, but unnecessarily, another hydrophobic region, extending from the amino acid residue at position 487 to the amino acid residue at position 514, could be deleted.

Similarly, the means needed for the synthesis of a soluble gp160 variant obviously include the corresponding DNA fragment, which must be obtained by modification of the original DNA fragment.

A comparison of the sequences of the different gp160 proteins already known has demonstrated at least three domains whose sequence is hypervariable from one gp160 to another. These three domains are commonly referred to as the $V_1$, $V_2$ and $V_3$ domains (or loops).

The first two domains, $V_1$ and $V_2$, are located between the cysteine residue at position 96 and the cysteine residue at position 171, while the third domain, $V_3$, is located from the cysteine residue at position 271 to the cysteine residue at position 306.

There is also a final domain exhibiting some degree of variability, albeit considered to be lesser. This is the site of binding to the CD4 receptor of T-helper lymphocytes; it being located approximately from the amino acid residue at position 340 to the amino acid residue at position 440.

Irrespective of the gp160 under consideration, vaccination experiments have shown that the third hyper-variable domain is essential for obtaining appropriate immunity. However, as a result of the hypervariable nature of this domain, the protection developed will be effective only against the viral strain from which the gp160 used is derived.

Lastly, it would appear that the first and the second hypervariable domains, as well as the CD4 receptor binding site, have an influence on the degree of immunity that could be obtained.

A vaccine of general applicability should enable individuals to be protected against the majority of HIV viral strains which are rife in the world. Consequently, a gp160-based vaccine should contain various gp160 proteins, each derived from a different viral strain. In order to employ such a vaccine, it is appropriate, in the first place, to construct the means intended for the production of the non-cleavable and soluble gp160 variant corresponding to each viral strain. As a first approach, this would hence involve cloning in each instance the DNA fragment coding for the gp160 of a particular viral strain, determining its sequence, modifying this DNA fragment in order to eliminate cleavage sites and hydrophobic regions by substitution or deletion and then, lastly, placing this DNA fragment thus modified in suitable conditions of expression. Since this type of operation would have to be repeated for each gp160, the preparation of such a vaccine is anticipated to be lengthy and expensive.

Furthermore, the viral strains can vary with the passage of time, e.g. by mutation. A particular strain which is a major cause of infection in a particular region of the world at a particular time can regress as an infectious agent, and another particular strain appear as a replacement. It is hence important to be able to adapt a vaccine rapidly to the epidemiological conditions and, in the present case, to have a gp160 variant available in the shortest possible time.

For this purpose, a new method has now been found for obtaining a gp160 variant which is suitable irrespective of the viral strain in question. Inasmuch as an expression cassette intended for the production of a non-cleavable and soluble gp160 variant derived from a first viral strain is made available, this method makes it possible to obtain a similar variant derived from a second viral strain while avoiding the complete cloning of the DNA fragment coding the gp160 of the second viral strain, and the modifications which would have to ensue therefrom.

Consequently, the invention proposes a method for constructing an expression cassette containing a DNA unit coding either for a precursor of a non-cleavable and soluble hybrid gp160 variant, or for a non-cleavable and soluble hybrid gp160 variant; said variant having an amino acid sequence comprising:

i) a first region derived from the gp160 of a first strain of HIV virus and located in this latter gp160 from the amino acid at position X to the amino acid at position Y, X being a number from 1 to 271 and Y being a number from 306 to 482;

ii) a second region derived from a type A non-cleavable, soluble gp160 variant originating from a second strain of HIV virus and located in this latter gp160 variant from the amino acid at position Y+1 to the amino acid at the C-terminal position, Y being as defined above; and iii) when X is other than 1, a third region derived from the gp160 of said second strain of HIV virus and located in this latter gp160 from the amino acid at position 1 to the amino acid at position X–1, X being as defined above;

said method comprising:

a) the act of cloning a DNA fragment coding for said first region; and b) the act of inserting the DNA fragment cloned in a) into a site of a cassette which comprises:

m) upstream of the site and in sequence:
   i) a promotor,
   ii) a translation initiation codon,
   iii) optionally, a first DNA region coding for a signal peptide, and
   iv) when X is as defined above but other than 1, a second DNA region coding for said third region of the amino acid sequence of said hybrid gp160 variant; and
n) downstream of the site and in sequence:
   i) when Y is as defined above, a third DNA region coding for said second region of the amino acid sequence of said hybrid gp160 variant, and
   ii) a translation termination codon;
to obtain an expression cassette containing said DNA unit.

Such an expression cassette is the indispensable tool which enables a soluble and non-cleavable hybrid gp160 variant to be produced in a heterologous expression system.

In the method according to the invention, the DNA fragment coding for said first region may be cloned according to any method in common use. It may be noted, however, that this cloning may be advantageously performed by the PCR technique starting with the genomic DNA of cells infected with said second strain of HIV virus. Insertion of the cloned DNA fragment takes place in restriction sites initially present in the cassette or created for this purpose, for example by the suitable use of a polylinker. An illustration of this method is presented below in the examples.

"DNA unit coding for a polypeptide of any kind" is understood to mean a DNA segment whose first codon at the 5' position and last codon at the 3' position code, respectively, for the first amino acid at the N-terminal position and the last amino acid at the C-terminal position of the polypeptide.

According to a preferred embodiment, the method according to the invention is carried out in order to construct an expression cassette containing a DNA unit coding for a precursor of a non-cleavable and soluble hybrid gp160 variant.

"Precursor of a gp160 variant according to the invention" means a polypeptide containing a signal peptide and a mature gp160 variant; the N-terminal end of said variant being combined with the C-terminal end of the signal peptide via a peptide bond. This precursor is the initial product of expression of the DNA unit. It is, in particular, present in the cytoplasm of the host cell, combined at the N-terminal position with a translation initiation methionine residue. The signal peptide enables the transfer of the gp160 variant to the endoplasmic reticulum to be initiated. During this transfer, the signal peptide is relinquished by proteolytic cleavage to give the mature form of the gp160 variant. In the remainder of the text, the term "gp160 variant" refers exclusively to its mature form.

The signal peptide can be any signal peptide in common use. It must, however, be chosen taking into account the host organism intended for the production of the gp160 variant according to the invention. For example, if the host organism is a mammalian cell, the signal peptide may be advantageously selected from the signal peptides of the precursors of the gp160 proteins of the different strains of HIV virus, independently of the origin of the first, second and third regions of the variant according to the invention. Alternatively, synthetic signal peptides may be used. Such signal peptides are, for example, hybrid signal peptides whose N-terminal end is derived from the precursor of the gp160 of said second strain of HIV virus and whose C-terminal end is derived from the precursor of the gp160 of said first strain of HIV virus. As a guide, it may be mentioned furthermore that the signal peptide of the precursor of the glycoprotein of a strain of the rabies virus may also be used. Lastly, a person skilled in the art should understand that this list is non-limiting.

The invention likewise proposes a non-cleavable and soluble hybrid gp160 variant which comprises:
   i) a first region derived from the gp160 of a first strain of HIV virus and located in this latter gp160 from the amino acid at position X to the amino acid at position Y, X being a number from 1 to 271 and Y being a number from 306 to 482;
   ii) a second region derived from a type A non-cleavable, soluble gp160 variant originating from a second strain of HIV virus and located in this latter gp160 variant from the amino acid at position Y+1 to the amino acid at the C-terminal position, Y being as defined above; and
   iii) when X is other than 1, a third region derived from the gp160 of said second strain of HIV virus and located in this latter gp160 from the amino acid at position 1 to the amino acid at position X–1, X being as defined above.

The first and also the second and third regions of the gp160 variant according to the invention may be derived from the gp160 of any strain of HIV virus, on condition that the first strain is different from the second. Preferably, the first region is derived from the gp160 of a viral strain selected from the strains HIV-2 Rod, HIV-1 Eli, HIV-1 RF, HIV-1 SF2C, HIV-1 SC and HIV-1 MN, the latter being more especially preferred. Similarly, the second and third regions preferably originate from the gp160 of the strain HIV-1 Bru.

"Type A non-cleavable gp160 variant" is understood to mean a gp160 variant:
   either derived from a gp160 of a type HIV-1 viral strain no longer containing the major cleavage site,
   or derived from a gp160 of a type HIV-2 viral strain no longer containing the cleavage site.

When the gp160 variant is derived from a gp160 of a type HIV-1 viral strain, this variant is preferably of type A'; that is to say, containing neither the major cleavage site nor the minor cleavage site.

"Soluble gp160 variant" is understood to mean a gp160 variant derived from a native gp160 which no longer contains a transmembrane region or whose native transmembrane region has been mutated so that it can no longer perform its function of anchorage in the membrane. In addition, it is advantageously possible for such a soluble variant no longer to contain a hydrophobic region.

"Expression cassette" is understood to mean a DNA segment comprising a DNA unit to be expressed, as well as the elements needed for expression of the latter. The expression of a DNA unit is obtained by transcription of this DNA unit into messenger RNA and by translation of this messenger RNA into protein. Consequently, the essential elements are a constitutive or inducible promoter (transcription initiation), a translation initiation codon (ATG codon) and a translation termination codon (TAG, TAA or TGA codon). In addition, an expression cassette can also contain other elements; for example, a transcription terminator.

A person skilled in the art is obviously capable of choosing the appropriate promoter and terminator in accordance with the host organism in which it is desired to express the DNA unit, and in accordance with the vector into which the expression cassette has to be inserted in order to provide for its replication.

In keeping with the foregoing, the invention likewise proposes an expression cassette containing a DNA unit coding either for a precursor of a gp160 variant according to the invention, or for a gp160 variant according to the invention, as well as the elements needed for expression of said DNA unit.

In order to provide for its autonomous application in a host organism, an expression cassette according to the invention may be inserted into different types of vector having an origin of replication suited to the host organism; for example a plasmid or a virus. Viral type vectors have, in particular, the capacity to integrate in their genome a substantial amount of foreign DNA without impairing their capacity for replication. These vectors include, for example, pox viruses such as vaccinia virus, canarypox virus and fowlpox virus; and baculoviruses such as adenoviruses such as Adenovirus-2 or Adenovirus-5.

Apart from their use in a heterologous production system, some of these viral type vectors can be functional as a vaccinating agent. This applies, in particular, to the pox viruses and adenoviruses.

Thus, the invention likewise relates to a viral vector, into the genome of which an expression cassette according to the invention is inserted.

In another aspect of the invention, a cell transformed with an expression cassette according to the invention is also obtained. The expression cassette which transforms the cell may be transported by a plasmid or, alternatively, be integrated in the genome of the host cell.

The host organism intended for the production of the gp160 variant according to the invention can be any type of cell, preferably eukaryotic. This includes, for example: fungi such as yeasts, insect cells and mammalian cells.

The invention proposes, in addition, two alternative processes directed towards the production of a gp160 variant according to the invention:

the first process comprises the act of culturing a cell according to the invention and the act of harvesting said variant from the culture, the second process comprises the act of infecting a cell culture with a viral vector according to the invention and the act of harvesting said variant from the culture.

A gp160 variant and also a viral vector according to the invention possess a vaccinal activity against an HIV virus, and are consequently useful as pharmaceutical products intended especially for the treatment or prevention of AIDS.

Consequently, the invention proposes:

i) a pharmaceutical composition intended for the curative or preventive treatment of AIDS, which comprises as therapeutic agent at least one gp160 variant or one viral vector according to the invention, ii) a method of curative or preventive treatment of AIDS, which comprises the act of administering a therapeutically effective amount of a gp160 variant or of a viral vector according to the invention to a patient needing such a treatment, iii) the use of a gp160 variant or of a viral vector according to the invention as therapeutic agent intended for the curative or preventative treatment of AIDS.

Preferably, a pharmaceutical composition according to the invention can contain several gp160 variants according to the invention; each gp160 variant possessing at least one third hypervariable domain ($V_3$ loop) different from the other variants present in the composition. Such a pharmaceutical composition should hence enable an individual to be correctly protected with respect to various HIV strains.

A pharmaceutical composition according to the invention can consist, in addition, of other therapeutic agents such as, for example, a peptide essentially corresponding to the third hypervariable domain of a gp160 (hereinafter referred to as $V_3$ peptide). Preferably, such a peptide has a sequence substantially identical to the sequence of the third domain of a gp160 variant contained in the pharmaceutical composition according to the invention. Similarly, several $V_3$ peptides may be present in the composition. In particular, if the pharmaceutical composition according to the invention contains different gp160 variants, the corresponding $V_3$ peptides can obviously be added thereto.

A pharmaceutical composition according to the invention may be manufactured in a conventional manner. In particular, a gp160 variant according to the invention is combined with a diluent or a vehicle which is acceptable from a pharmaceutical standpoint. Lastly, a composition according to the invention can contain a vaccination adjuvant such as alum. Alternatively, this adjuvant may be added to a composition according to the invention immediately before use.

A composition according to the invention may be administered by any conventional route in common use in the vaccine field, especially subcutaneously, for example in the form of an injectable solution or suspension. The administration can take place in a single dose or a dose repeated one or more times after a certain time interval. The appropriate dosage varies in accordance with various parameters, for example with the individual being treated or the mode of administration.

Alternatively, a pharmaceutical composition according to the invention may be presented as part of a treatment kit. As an example, it may be noted that such a kit can contain:

on the one hand a pharmaceutical composition containing at least one gp160 variant according to the invention, and on the other hand a pharmaceutical composition containing at least one $V_3$ peptide, as well as a leaflet specifying the instructions relating to the sequential or concomitant administration of the pharmaceutical compositions contained in the kit.

The invention is illustrated below by reference to the following figures:

FIG. 1 [SEQ ID NOS.:10–15] presents the amino acid sequence of the precursors of the native gp160 proteins of the viral strains HIV-1 Bru (a), HIV-1 MN (b), HIV-1 Eli (c), HIV-1 RF (d), HIV-1 SC (e), and HIV-1 SF2C (f). The amino acid residues of the signal sequences are numbered from position −1 to −29. The methionine residue at position −30 corresponds to the translation initiation codon. The amino acid residues of the mature gp160 proteins are numbered from position 1 to 841. The asterisk (*) symbolizes the identity of the amino acid residues at a given position, while the dot (.) indicates a conservative change (different amino acids but belonging to the same class).

FIG. 2 [SEQ ID NOS.:16–17] presents the amino acid sequence of the precursors of the native gp160 proteins of the viral strains HIV-1 Bru (a) and HIV-2 Rod (b). The amino acid residues of the signal sequences are numbered from position −1 to −29. The methionine residue at position −30 corresponds to the translation initiation codon. The amino acid residues of the mature gp160 proteins are numbered from position 1 to 841. The asterisk (*) symbolizes the identity of the amino acid residues at a given position, while the dot (.) indicates a conservative change (different amino acids but belonging to the same class).

FIG. 3 [SEQ ID NOS.:18–20] presents the nucleotide sequence of the PstI—PstI fragment of the vector pTG1163 which contains the sequence coding for a precursor of a soluble, non-cleavable gp160-Bru variant (transmembrane domain absent), as well as the amino acid sequence of this precursor.

FIG. 4 shows diagrammatically the steps in the construction of the bacteriophages M13TG4168 and M13TG4174.

FIG. 5 [SEQ ID NOS.:21–23] presents the nucleotide sequence coding for the precursor of gp120-MN, as well as the amino acid sequence of this precursor. The oligonucleotides OTG2624 and OTG2625, intended for the amplification of a DNA fragment coding at least for the third hypervariable domain of gp120-MN, are shown above their hybridization region.

FIG. 6 [SEQ ID NO.:24] presents the nucleotide sequence coding for the precursor of gp120-Eli, as well as the amino acid sequence of this precursor. The oligonucleotides OTG2624 and OTG2625, intended for the amplification of a DNA fragment coding at least for the third hypervariable domain of gp120-MN, are shown above their hybridization region.

FIG. 7 [SEQ ID NO.:25] presents the nucleotide sequence coding for the precursor of gp120-RF, as well as the amino acid sequence of this precursor. The oligonucleotides OTG2624 and OTG2625, intended for the amplification of a DNA fragment coding at least for the third hypervariable domain of gp120-RF, are shown above their hybridization region.

FIG. 8 [SEQ ID NO.:26] presents the nucleotide sequence coding for the precursor of gp120-SF2C, as well as the amino acid sequence of this precursor. The oligonucleotides OTG2624 and OTG2625, intended for the amplification of a DNA fragment coding at least for the third hypervariable domain of gp120-SF2C, are shown above their hybridization region.

In the examples which follow, to make the text easier to write and to understand, "signal sequence" is understood to mean a signal sequence including the translation initiation methionine residue.

EXAMPLE 1
Construction of an Insertion Cassette Carried by the Bacteriophage M13TG4168.

As shown in SEQ. ID NOS.: 9–12 the PstI—PstI DNA fragment of plasmid pTG1163 described in Patent Application EPA 245, 136 contains a DNA sequence coding for a precursor of a non-cleavable and soluble gp160-Bru variant. This PstI—PstI DNA fragment is inserted into the bacteriophage M13mp701 (described by M. P. Kieny et al. Gene (1983) 26:91) previously digested with PstI, to give the bacteriophage M13TG4137. The numbering of the nucleotides of the PstI—PstI fragment as shown in SEQ ID NOS.: 9–12 serves as a reference in the remainder of Example 1.

Plasmid pTG1163 is cut with PstI and KpnI, and the DNA fragment corresponding to nucleotides 1 to 138 SEQ ID NOS.: 9–12 is inserted into the bacteriophage M13TG130 (described by M. P. Kieny et al. (1983), supra) previously digested with PstI and KpnI. The bacteriophage M13TG4147 is thereby obtained.

The bacteriophage M13TG4137 is cut with BglII, treated with the Klenow enzyme (Boehringer Mannheim) to obtain blunt ends and then cut with EcoRI. The EcoRI-BglII° fragment derived from this digestion and containing the sequence corresponding to nucleotides 1424 to 2644 SEQ ID NOS.: 9–12 is inserted into the bacteriophage M13TG4147 previously digested with EcoRV and EcoRI. The bacteriophage M13TG4158, which contains:

i) a DNA fragment corresponding to nucleotides 1 to 138, ii) the remaining sequence [SEQ ID NO.:5] of the polylinker of the bacteriophage M13TG4147, that is to say ATCGCATGCG, iii) a DNA fragment corresponding to nucleotides 1424 to 2644, is thereby obtained.

The single-stranded antisense bacteriophage M13TG4158 serves as a template for a mutation-deletion, performed using the Amersham kit and the oligonucleotide OTG2623 whose sequence [SEQ ID NO.:6] is as follows:

This mutagenesis makes it possible simultaneously to delete a 184-base pair fragment which contains nucleotides 67 to 138, the sequence [SEQ ID NO.:5] ATCGCATGCG and nucleotides 1424 to 1525, and to create the cleavage sites for the enzymes SphI at the 5' end and SmaI at the 3' end, which are inserted between nucleotides 66 and 1526. The bacteriophage M13TG4168, which comprises:

i) a DNA fragment corresponding to nucleotides 1 to 66, ii) the DNA sequence [SEQ ID NO.:7] GCATGCATCCCG containing the cleavages sites of the enzymes SphI and SmaI, and iii) a DNA fragment corresponding to nucleotides 1526 to 2644, is thereby obtained.

EXAMPLE 2
Construction of an Expression Cassette Intended for the Synthesis of a Bru-MN Hybrid gp160 Variant.

As shown in SEQ ID NOS.: 13–14 the DNA fragment coding for the larger part of a precursor of gp120-MN is cloned by the PCR (Polymerase Chain Reaction) gene amplification technique, carried out starting with genomic DNA of CEM human cells infected with the viral strain HIV1-MN. This cloning is performed using the oligonucleotides OTG2624 and OTG2625, which introduce, respectively, a cleavage site for the enzyme SphI at the 5' end of the amplified DNA fragment and a cleavage site for the enzyme SmaI at the 3' end of the amplified DNA fragment. The sequences [SEQ ID NOS.:8–9] of these oligonucleotides are as follows:

```
                 SphI
                ┌──────┐
OTG2624 : GGCA GCATGC TCCTTGGGATATTGATGATCTG

SmaI
                ┌──────┐
OTG2625 : CTTTG CCCGGG TGGGTGCTACTCCTAATGGTTC
```

The amplified SphI-SmaI DNA fragment corresponds to nucleotides 53 to 1505 shown in SEQ ID NOS.: 13–14, taking into account the sequence modifications brought about by the oligonucleotides OTG2624 and OTG2625. This fragment is inserted into the bacteriophage M13TG4168 cut with SphI and SmaI. The bacteriophage M13TG4174, which contains a DNA fragment coding for a precursor of a Bru-MN hybrid gp160 protein, is thereby obtained. The PstI fragment of the bacteriophage M13TG4174 which codes for the Bru-MN hybrid gp160 variant is inserted into the transfer plasmid pTG186poly (described by M. P. Kieny et al., Biotechnology, (1986) 4: 790), downstream of the E7.5k promoter and within the vaccinia virus gene coding for thymidine kinase. Plasmid pTG5156 is thereby obtained.

Plasmid pTG5156 is subsequently used to transfer the block for expression of the Bru-MN hybrid gp160 protein into the genome of vaccinia virus, Copenhagen strain, according to the method described by M. P. Kieny et al. Nature (1984), 312, 163–166). The vaccinia vector VVTG5156 is thereby obtained.

EXAMPLE 3

Construction of an Expression Cassette Intended for the Synthesis of a Bru-Eli Hybrid gp160 Variant.

Plasmid pTG186poly is cut with BamHI, treated with the Klenow enzyme, cut with SmaI to delete the larger part of the polylinker and then religated with itself to give plasmid pTG186PE. The polylinker now retains only the cleavage sites for the enzymes PstI, SalI and EcoRI.

The PstI—PstI DNA fragment of the bacteriophage M13TG4168 described above, which contains:

i) a DNA fragment corresponding to nucleotides 1 to 66 of the DNA fragment shown in SEQ ID NOS.: 9–12, ii) the DNA sequence [SEQ ID NO.:7] GCATGCATC-CCG containing the cleavage sites of the enzymes SphI and SmaI, and iii) a DNA fragment corresponding to nucleotides 1526 to 2644 of the DNA fragment shown in SEQ ID NOS.: 9–12, is inserted into plasmid pTG186PE previously cut with PstI, downstream of the E7.5k promoter and within the vaccinia virus gene coding for thymidine kinase. Plasmid pTG5160 is thereby obtained.

As shown in SEQ ID NOS.: 15–16, the DNA fragment coding for the larger part of a precursor of gp120-Eli is cloned by the PCR gene amplification technique, carried out starting with the genomic DNA of CEM human cells infected with HIV1-Eli virus. This cloning is performed using the oligonucleotides OTG2624 and OTG2625, which introduce, respectively, a cleavage site for the enzyme SphI at the 5' end of the amplified DNA fragment and a cleavage site for the enzyme SmaI at the 3' end of the amplified DNA fragment. The amplified SphI-SmaI DNA fragment corresponds to nucleotides 53 to 1490 shown in SEQ ID NOS.: 15–16, taking into account the sequence modifications brought about by the oligonucleotides OTG2624 and OTG2625. This fragment is inserted into the bacteriophage M13TG131 (described by M. P. Kieny et al. (1983), supra) previously cut with SphI and SmaI, to give the bacteriophage M13TG4197. The SphI-SmaI fragment of the bacteriophage M13TG4197 is then inserted into the transfer plasmid pTG5160 (described above) previously cut with SphI and SmaI. pTG5193 is thereby obtained.

Plasmid pTG5193 is subsequently used to transfer the block for expression of the Bru-Eli hybrid gp160 protein into the genome of vaccinia virus, Copenhagen strain, according to the method described by M. P. Kieny et al. (1984) supra. The vaccinia vector VVTG5193 is thereby obtained.

EXAMPLE 4

Construction of an Expression Cassette Intended for the Synthesis of a Bru-RF Hybrid gp160 Variant.

As shown in SEQ ID NOS.: 17–18, the DNA fragment coding for the larger part of a precursor of a gp120-RF protein is cloned by the PCR gene amplification technique, carried out starting with the genomic DNA of CEM human cells infected with HIV1-RF virus. This cloning is performed using the oligonucleotides OTG2624 and OTG2625, which introduce, respectively, a cleavage site for the enzyme SphI at the 5' end of the amplified DNA fragment and a cleavage site for the enzyme SmaI at the 3' end of the amplified DNA fragment. The amplified SphI-SmaI DNA fragment corresponds to nucleotides 53 to 1523 shown in SEQ ID NOS.: 17–18, taking into account the sequence modifications brought about by the oligonucleotides OTG2624 and OTG2625. This fragment is inserted into the bacteriophage M13TG131 previously cut with SphI and SmaI, to give the bacteriophage M13TG4198. The SphI-SmaI fragment of the bacteriophage M13TG4198 is then inserted into the transfer plasmid pTG5160 (described in Example 3) previously cut with SphI and SmaI. pTG5194 is thereby obtained.

Plasmid pTG5194 is subsequently used to transfer the block for expression of the Bru-RF hybrid gp160 protein into the genome of vaccinia virus, Copenhagen strain, according to the method described by M. P. Kieny et al. (1984) supra. The vaccinia vector VVTG5194 is thereby obtained.

EXAMPLE 5

Construction of an Expression Cassette Intended for the Synthesis of a Bru-SF2C Hybrid gp160 Variant.

As shown in SEQ ID NOS.: 19–20, the DNA fragment coding for the larger part of a precursor of gp120-SF2C is cloned by the PCR gene amplification technique, carried out starting with the genomic DNA of CEM human cells infected with HIV1-SF2C virus. This cloning is performed using the oligonucleotides OTG2624 and OTG2625, which introduce, respectively, a cleavage site for the enzyme SphI at the 5' end of the amplified DNA fragment and a cleavage site for the enzyme SmaI at the 3' end of the amplified DNA fragment. The amplified SphI-SmaI DNA fragment corresponds to nucleotides 53 to 1493 shown in SEQ ID NOS.: 19–20, taking into account the sequence modifications brought about by the oligonucleotides OTG2624 and OTG2625. This fragment is then inserted into the bacteriophage M13TG131 previously cut with SphI and SmaI, to give the bacteriophage M13TG4199. The SphI-SmaI fragment of the bacteriophage M13TG4199 is inserted into the transfer plasmid pTG5160 (described in Example 3) previously cut with SphI and SmaI. pTG5195 is thereby obtained.

Plasmid pTG5195 is subsequently used to transfer the block for expression of the Bru-SF2C hybrid gp160 protein into the genome of vaccinia virus, Copenhagen strain, according to the method described by M. P. Kieny et al. (1984) supra. The vaccinia vector VVTG5195 is thereby obtained.

EXAMPLES 6 to 9

Production and Purification of Bru-MN, Bru-Eli, Bru-RF and Bru SF2C Hybrid gp160 Proteins:

BHK-21 cells are cultured in a GMEM medium (Gibco) supplemented with 10 % of fetal calf serum (FCS). When the cells are at confluence ($5.8 \times 10^6$ cells/ml), the culture medium is removed and the cell lawn is washed twice with 50 ml of PBS (Dubelcco's phosphate buffer salt; Seromed). Fresh GMEM medium without FCS is then added. One of the vaccinia viruses VVTG5156, VVTG5193, VVTG5194 and VVTG5195, described above in Examples 2 to 5, is then added at an infectivity of 1 pfu/cell (plaque forming unit), and infection is continued for 72 h. The lysate is then centrifuged for 20 min at 10,000 g in order to remove cell debris, and the supernatant containing, inter alia, a hybrid gp160 and virions is recovered.

To 20 ml of culture supernatant obtained as described above, 1.3 ml of 1 M zinc chloride ($ZnCl_2$) solution is added so as to have a final $ZnCl_2$ concentration of 60 mM. The mixture is left for 1 h in ice; the precipitation supernatant is then recovered after centrifugation at 3000 rpm for 20 min in a Heraeus RF Minifuge centrifuge. This method removes by precipitation the virions as well as the majority of contaminant proteins. In each case, a purified solution of the hybrid gp160 variant is thereby obtained.

I claim:

1. A method for constructing a human immunodeficiency virus type 1 (HIV-1) gp160 expression cassette, wherein said expression cassette contains a nucleic acid capable of encoding a soluble, non-cleavable, chimeric HIV-1 gp160 variant, said variant comprising the following regions:

i) a first region derived from the gp160 of a first strain of HIV-1 consisting of amino acids X to Y, wherein X is a number from 1 to 271 and Y is a number from 306 to 482;

ii) a second region derived from the gp160 of a second strain of HIV-1 consisting of amino acids Y+1 to the carboxyl terminus of the envelope, wherein said second region fails to contain functional major and minor proteolytic cleavage sites (amino acids 483–486 and 475–479, respectively) and functional major and minor hydrophobic domains (amino acids 487–516 and 659–680, respectively); and iii) an optional third region, present when X is greater than 1, said region derived from the gp160 of said second strain of HIV-1 and consisting of amino acids 1 to X−1, wherein the numbering scheme of X and Y is based upon the numbering scheme of the HIV-1 isolate BRU; said method comprising the following steps:

i) cloning and isolating DNA fragments encoding said first, second, and third regions of the HIV-1 envelope;

ii) inserting said DNA fragments into an appropriate site in an expression cassette, wherein said cassette comprises a promoter, translation initiation codon, and optional nucleic acid encoding a signal peptide in sequence and upstream of the insertion site, and a translation termination site downstream of the insertion site.

2. The method according to claim 1, wherein said expression cassette contains a nucleic acid sequence encoding a signal peptide fused to the inserted DNA fragments encoding said first, second, and third regions of the HIV-1 envelope.

3. The method according to claim 1, wherein said second strain of HIV-1 is selected from the group of HIV-1 strains consisting of BRU and MN.

4. The method according to claim 1, wherein said first strain of HIV-1 is selected from the group of HIV-1 strains consisting of MN, ELI, RF, SF2C, and SC.

5. An expression cassette containing a nucleic acid capable of encoding a soluble, non-cleavable, chimeric HIV-1 gp160 variant, said variant comprising the following regions:

i) a first region derived from the gp160 of a first strain of HIV-1 consisting of amino acids X to Y, wherein X is a number from 1 to 271 and Y is a number from 306 to 482;

ii) a second region derived from the gp160 of a second strain of HIV-1 consisting of amino acids Y+1 to the carboxyl terminus of the envelope, wherein said second region fails to contain functional major and minor proteolytic cleavage sites (amino acids 483–486 and 475–479, respectively) and functional major and minor hydrophobic domains (amino acids 487–516 and 659–680, respectively); and iii) an optional third region, present when X is greater than 1, said region derived from the gp160 of said second strain of HIV-1 and consisting of amino acids 1 to X−1, wherein the numbering scheme of X and Y is based upon the numbering scheme of the HIV-1 isolate BRU; said expression cassette further comprising:

i) a promoter, translation initiation codon, and optional nucleic acid encoding a signal peptide in sequence and upstream of the insertion site, and a translation termination site downstream of the insertion site.

6. The expression cassette according to claim 5, wherein said expression cassette contains a nucleic acid sequence encoding a signal peptide fused to the amino terminus of said first, second, and third regions of the HIV-1 envelope.

7. The expression cassette according to claim 5, wherein said second strain of HIV-1 is selected from the group of HIV-1 strains consisting of BRU and MN.

8. The expression cassette according to claim 5, wherein said first strain of HIV-1 is selected from the group of HIV-1 strains consisting of MN, ELI, RF, SF2C, and SC.

9. A method for constructing a human immunodeficiency virus type 1 (HIV-1) gp160 expression cassette, wherein said expression cassette contains a nucleic acid capable of encoding a soluble, non-cleavable, chimeric HIV-1 gp160 variant, said variant comprising the following regions:

i) a first region derived from the gp160 of a first strain of HIV-1 consisting of amino acids X to Y, wherein X is a number from 1 to 271 and Y is a number from 306 to 476;

ii) a second region derived from the gp160 of a second strain of HIV-1 consisting of amino acids Y+1 to the carboxyl terminus of the envelope, wherein said second region fails to contain functional major and minor proteolytic cleavage sites (amino acids 483–486 and 475–479, respectively) and functional major and minor hydrophobic domains (amino acids 487–516 and 659–680, respectively); and iii) an optional third region, present when X is greater than 1, said region derived from the gp160 of said second strain of HIV-1 and consisting of amino acids 1 to X−1, wherein the numbering scheme of X and Y is based upon the numbering scheme of the HIV-1 isolate BRU; said method comprising the following steps:

i) cloning and isolating DNA fragments encoding said first, second, and third regions of the HIV-1 envelope;

ii) inserting said DNA fragments into an appropriate site in an expression cassette, wherein said cassette comprises a promoter, translation initiation codon, and optional nucleic acid encoding a signal peptide in sequence and upstream of the insertion site, and a translation termination site downstream of the insertion site.

10. The method according to claim 9, wherein said expression cassette contains a nucleic acid sequence encoding a signal peptide fused to the inserted DNA fragments encoding said first, second, and third regions of the HIV-1 envelope.

11. The method according to claim 9, wherein said second strain of HIV-1 is selected from the group of HIV-1 strains consisting of BRU and MN.

12. The method according to claim 9, wherein said first strain of HIV-1 is selected from the group of HIV-1 strains consisting of MN, ELI, RF, SF2C, and SC.

13. An expression cassette containing a nucleic acid capable of encoding a soluble, non-cleavable, chimeric HIV-1 gp160 variant, said variant comprising the following regions:
   i) a first region derived from the gp160 of a first strain of HIV-1 consisting of amino acids X to Y, wherein S is a number from 1 to 271 and Y is a number from 306 to 476;
   ii) a second region derived from the gp160 of a second strain of HIV-1 consisting of amino acids Y+1 to the carboxyl terminus of the envelope, wherein said second region fails to contain functional major and minor proteolytic cleavage sites (amino acids 483–486 and 475–479, respectively) and functional major and minor hydrophobic domains (amino acids 487–516 and 659–680, respectively); and
   iii) an optional third region, present when X is greater than 1, said region derived from the gp160 of said second strain of HIV-1 and consisting of amino acids 1 to X−1,
      wherein the numbering scheme of X and Y is based upon the numbering scheme of the HIV-1 isolate BRU; said expression cassette further comprising:
         i) a promoter, translation initiation codon, and optional nucleic acid encoding a signal peptide in sequence and upstream of the insertion site, and a translation termination site downstream of the insertion site.

14. The expression cassette according to claim 13, wherein said expression cassette contains a nucleic acid sequence encoding a signal peptide fused to the amino terminus of said first, second, and third regions of the HIV-1 envelope.

15. The expression cassette according to claim 13, wherein said second strain of HIV-1 is selected from the group of HIV-1 strains consisting of BRU and MN.

16. The expression cassette according to claim 13, wherein said first strain of HIV-1 is selected from the group of HIV-1 strains consisting of MN, ELI, RF, SF2C, and SC.

17. A method for constructing a human immunodeficiency virus type 1 (HIV-1) gp160 expression cassette, wherein said expression cassette contains a nucleic acid capable of encoding a soluble, non-cleavable, chimeric HIV-1 gp160 variant, said variant comprising the following regions:
   i) a first region derived from the gp160 of a first strain of HIV-1 consisting of amino acids X to Y, wherein X is a number from 1 to 271 and Y is a number from 450 to 482;
   ii) a second region derived from the gp160 of a second strain of HIV-1 consisting of amino acids Y+1 to the carboxyl terminus of the envelope, wherein said second region fails to contain functional major and minor proteolytic cleavage sites (amino acids 483–486 and 475–479, respectively) and functional major and minor hydrophobic domains (amino acids 487–516 and 659–680, respectively); and
   iii) an optional third region, present when X is greater than 1, said region derived from the gp160 of said second strain of HIV-1 and consisting of amino acids 1 to X−1,
      wherein the numbering scheme of X and Y is based upon the numbering scheme of the HIV-1 isolate BRU; said method comprising the following steps:
         i) cloning and isolating DNA fragments encoding said first, second, and third regions of the HIV-1 envelope;
         ii) inserting said DNA fragments into an appropriate site in an expression cassette, wherein said cassette comprises a promoter, translation initiation codon, and optional nucleic acid encoding a signal peptide in sequence and upstream of the insertion site, and a translation termination site downstream of the insertion site.

18. The method of claim 17, wherein said expression cassette contains a nucleic acid sequence encoding a signal peptide fused to the inserted DNA fragments encoding said first, second, and third regions of the HIV-1 envelope.

19. The method according to claim 17, wherein said second strain of HIV-1 is selected from the group of HIV-1 strains consisting of BRU and MN.

20. The method according to claim 17, wherein said first strain of HIV-1 is selected from the group of HIV-1 strains consisting of MN, ELI, RF, SF2C, and SC.

21. An expression cassette containing a nucleic acid capable of encoding a soluble, non-cleavable, chimeric HIV-1 gp160 variant, said variant comprising the following regions:
   i) a first region derived from the gp160 of a first strain of HIV-1 consisting of amino acids X to Y, wherein X is a number from 1 to 271 and Y is a number from 450 to 482;
   ii) a second region derived from the gp160 of a second strain of HIV-1 consisting of amino acids Y+1 to the carboxyl terminus of the envelope, wherein said second region fails to contain functional major and minor proteolytic cleavage sites (amino acids 483–486 and 475–479, respectively) and functional major and minor hydrophobic domains (amino acids 487–516 and 659–680, respectively); and
   iii) an optional third region, present when X is greater than 1, said region derived from the gp160 of said second strain of HIV-1 and consisting of amino acids 1 to X−1,
      wherein the numbering scheme of X and Y is based upon the numbering scheme of the HIV-1 isolate BRU; said expression cassette further comprising:
         i) a promoter, translation initiation codon, and optional nucleic acid encoding a signal peptide in sequence and upstream of the insertion site, and a translation termination site downstream of the insertion site.

22. The expression cassette according to claim 21, wherein said expression cassette contains a nucleic acid sequence encoding a signal peptide fused to the amino terminus of said first, second, and third regions of the HIV-1 envelope.

23. The expression cassette according to claim 21, wherein said second strain of HIV-1 is selected from the group of HIV-1 strains consisting of BRU and MN.

24. The expression cassette according to claim 21, wherein said first strain of HIV-1 is selected from the group of HIV-1 strains consisting of MN, ELI, RF, SF2C, and SC.

25. A method for constructing a human immunodeficiency virus type 1 (HIV-1) gp160 expression cassette, wherein said expression cassette contains a nucleic acid capable of encoding a soluble, non-cleavable, chimeric HIV-1 gp160 variant, said variant comprising the following regions:
 i) a first region derived from the gp160 of a first strain of HIV-1 consisting of amino acids X to Y, wherein X is a number from 1 to 97 and Y is a number from 306 to 482;
 ii) a second region derived from the gp160 of a second strain of HIV-1 consisting of amino acids Y+1 to the carboxyl terminus of the envelope, wherein said second region fails to contain functional major and minor proteolytic cleavage sites (amino acids 483–486 and 475–479, respectively) and functional major and minor hydrophobic domains (amino acids 487–516 and 659–680, respectively); and
 iii) an optional third region, present when X is greater than 1, said region derived from the gp160 of said second strain of HIV-1 and consisting of amino acids 1 to X−1,
  wherein the numbering scheme of X and Y is based upon the numbering scheme of the HIV-1 isolate BRU; said method comprising the following steps:
   i) cloning and isolating DNA fragments encoding said first, second, and third regions of the HIV-1 envelope;
   ii) inserting said DNA fragments into an appropriate site in an expression cassette, wherein said cassette comprises a promoter, translation initiation codon, and optional nucleic acid encoding a signal peptide in sequence and upstream of the insertion site, and a translation termination site downstream of the insertion site.

26. The method according to claim 25, wherein said expression cassette contains a nucleic acid sequence encoding a signal peptide fused to the inserted DNA fragments encoding said first, second, and third regions of the HIV-1 envelope.

27. The method according to claim 25, wherein said second strain of HIV-1 is selected from the group of HIV-1 strains consisting of BRU and MN.

28. The method according to claim 25, wherein said first strain of HIV-1 is selected from the group of HIV-1 strains consisting of MN, ELI, RF, SF2C, and SC.

29. An expression cassette containing a nucleic acid capable of encoding a soluble, non-cleavable, chimeric HIV-1 gp160 variant, said variant comprising the following regions:
 i) a first region derived from the gp160 of a first strain of HIV-1 consisting of amino acids X to Y, wherein X is a number from 1 to 97 and Y is a number from 306 to 482;
 ii) a second region derived from the gp160 of a second strain of HIV-1 consisting of amino acids Y+1 to the carboxyl terminus of the envelope, wherein said second region fails to contain functional major and minor proteolytic cleavage sites (amino acids 483–486 and 475–479, respectively) and functional major and minor hydrophobic domains (amino acids 487–516 and 659–680, respectively); and
 iii) an optional third region, present when X is greater than 1, said region derived from the gp160 of said second strain of HIV-1 and consisting of amino acids 1 to X−1,
  wherein the numbering scheme of X and Y is based upon the numbering scheme of the HIV-1 isolate BRU; said expression cassette further comprising:
   i) a promoter, translation initiation codon, and optional nucleic acid encoding a signal peptide in sequence and upstream of the insertion site, and a translation termination site downstream of the insertion site.

30. The expression cassette according to claim 29, wherein said expression cassette contains a nucleic acid sequence encoding a signal peptide fused to the amino terminus of said first, second, and third regions of the HIV-1 envelope.

31. The expression cassette according to claim 29, wherein said second strain of HIV-1 is selected from the group of HIV-1 strains consisting of BRU and MN.

32. The expression cassette according to claim 29, wherein said first strain of HIV-1 is selected from the group of HIV-1 strains consisting of MN, ELI, RF, SF2C, and SC.

33. A viral vector which contains an expression cassette according to claim 5.

34. A cell transfected with a viral vector according to claim 33.

35. A method of using the cell of claim 34 to produce a soluble, non-cleavable, chimeric HIV-1 gp160 variant comprising culturing said cell under conditions that provide for expression of said variant, and harvesting said variant from the cell culture.

36. A viral vector which contains an expression cassette according to claim 21.

37. A cell transfected with a viral vector according to claim 36.

38. A method of using the cell of claim 37 to produce a soluble, non-clcavable, chimeric HIV-1 gp160 variant comprising culturing said cell under conditions that provide for expression of said variant, and harvesting said variant from the cell culture.

39. A viral vector which contains an expression cassette according to claim 29.

40. A cell transfected with a viral vector according to claim 39.

41. A method of using the cell of claim 40 to produce a soluble, non-cleavable, chimeric HIV-1 gp160 variant comprising culturing said cell under conditions that provide for expression of said variant, and harvesting said variant from the cell culture.

42. A viral vector which contains an expression cassette according to claim 13.

43. A cell transfected with a viral vector according to claim 42.

44. A method of using the cell of claim 43 to produce a soluble, non-cleavable, chimeric HIV-1 gp160 variant comprising culturing said cell under conditions that provide for expression of said variant, and harvesting said variant from the cell culture.

* * * * *

```
                         SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: DNA (genomic)

(xi) SEQUENCE DESCRIPTION: SEQ ID NO:1:

Arg Glu Lys Arg
1

(2) INFORMATION FOR SEQ ID NO:2:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: DNA (genomic)

(xi) SEQUENCE DESCRIPTION: SEQ ID NO:2:

Lys Ala Lys Arg
1

(2) INFORMATION FOR SEQ ID NO:3:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: DNA (genomic)

(xi) SEQUENCE DESCRIPTION: SEQ ID NO:3:

Lys Glu Arg Lys
1

(2) INFORMATION FOR SEQ ID NO:4:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: DNA (genomic)

(xi) SEQUENCE DESCRIPTION: SEQ ID NO:4:
```

Asn Glu His Gln
1

(2) INFORMATION FOR SEQ ID NO:5:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

ATCGCATGCG                                                            10

(2) INFORMATION FOR SEQ ID NO:6:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GGGGGTGGAA ATGGGGCAGC ATGCATCCCG GGCACAGAAT CACGTGGTGC          50

(2) INFORMATION FOR SEQ ID NO:7:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GCATGCATCC CG                                                     12

(2) INFORMATION FOR SEQ ID NO:8:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GGCAGCATGC TCCTTGGGAT ATTGATGATC TG                        32

(2) INFORMATION FOR SEQ ID NO:9:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

CTTTGCCCGG GTGGGTGCTA CTCCTAATGG TTC                       33

(2) INFORMATION FOR SEQ ID NO:10:

(i) SEQUENCE CHARACTERISTICS:
        (A) LENGTH: 861 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
Met Arg Val Lys Glu Lys Tyr Gln His Leu Trp Arg Trp Gly Trp Lys
 1               5                  10                  15

Trp Gly Thr Met Leu Leu Gly Ile Leu Met Ile Cys Ser Ala Thr Glu
                20                  25                  30

Lys Leu Trp Val Thr Val Tyr Tyr Gly Val Pro Val Trp Lys Glu Ala
            35                  40                  45

Thr Thr Thr Leu Phe Cys Ala Ser Asp Ala Lys Ala Tyr Asp Thr Glu
        50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
                100                 105                 110

Asp Gln Ser Leu Lys Pro Cys Val Lys Leu Thr Pro Leu Cys Val Ser
            115                 120                 125

Leu Lys Cys Thr Asp Leu Gly Asn Ala Thr Asn Thr Asn Ser Ser Asn
130                 135                 140

Thr Asn Ser Ser Ser Gly Glu Met Met Met Glu Lys Gly Glu Ile Lys
145                 150                 155                 160

Asn Cys Ser Phe Asn Ile Ser Thr Ser Ile Arg Gly Lys Val Gln Lys
                165                 170                 175

Glu Tyr Ala Phe Phe Tyr Lys Leu Asp Ile Ile Pro Ile Asp Asn Asp
            180                 185                 190

Thr Thr Ser Tyr Thr Leu Thr Ser Cys Asn Thr Ser Val Ile Thr Gln
        195                 200                 205

Ala Cys Pro Lys Val Ser Phe Glu Pro Ile Pro Ile His Tyr Cys Ala
210                 215                 220

Pro Ala Gly Phe Ala Ile Leu Lys Cys Asn Asn Lys Thr Phe Asn Gly
225                 230                 235                 240

Thr Gly Pro Cys Thr Asn Val Ser Thr Val Gln Cys Thr His Gly Ile
                245                 250                 255

Arg Pro Val Val Ser Thr Gln Leu Leu Leu Asn Gly Ser Leu Ala Glu
            260                 265                 270

Glu Glu Val Val Ile Arg Ser Ala Asn Phe Thr Asp Asn Ala Lys Thr
        275                 280                 285

Ile Ile Val Gln Leu Asn Gln Ser Val Glu Ile Asn Cys Thr Arg Pro
290                 295                 300

Asn Asn Asn Thr Arg Lys Ser Ile Arg Ile Gln Arg Gly Pro Gly Arg
305                 310                 315                 320

Ala Phe Val Thr Ile Gly Lys Ile Gly Asn Met Arg Gln Ala His Cys
                325                 330                 335

Asn Ile Ser Arg Ala Lys Trp Asn Ala Thr Leu Lys Gln Ile Ala Ser
            340                 345                 350
```

-continued

```
Lys Leu Arg Glu Gln Phe Gly Asn Asn Lys Thr Ile Ile Phe Lys Gln
            355                 360                 365

Ser Ser Gly Gly Asp Pro Glu Ile Val Thr His Ser Phe Asn Cys Gly
    370                 375                 380

Gly Glu Phe Phe Tyr Cys Asn Ser Thr Gln Leu Phe Asn Ser Thr Trp
385                 390                 395                 400

Phe Asn Ser Thr Trp Ser Thr Glu Gly Ser Asn Asn Thr Glu Gly Ser
            405                 410                 415

Asp Thr Ile Thr Leu Pro Cys Arg Ile Lys Gln Phe Ile Asn Met Trp
            420                 425                 430

Gln Glu Val Gly Lys Ala Met Tyr Ala Pro Pro Ile Ser Gly Gln Ile
            435                 440                 445

Arg Cys Ser Ser Asn Ile Thr Gly Leu Leu Leu Thr Arg Asp Gly Gly
    450                 455                 460

Asn Asn Asn Asn Gly Ser Glu Ile Phe Arg Pro Gly Gly Gly Asp Met
465                 470                 475                 480

Arg Asp Asn Trp Arg Ser Glu Leu Tyr Lys Tyr Lys Val Val Lys Ile
            485                 490                 495

Glu Pro Leu Gly Val Ala Pro Thr Lys Ala Lys Arg Arg Val Val Gln
            500                 505                 510

Arg Glu Lys Arg Ala Val Gly Ile Gly Ala Leu Phe Leu Gly Phe Leu
            515                 520                 525

Gly Ala Ala Gly Ser Thr Met Gly Ala Arg Ser Met Thr Leu Thr Val
    530                 535                 540

Gln Ala Arg Gln Leu Leu Ser Gly Ile Val Gln Gln Gln Asn Asn Leu
545                 550                 555                 560

Leu Arg Ala Ile Glu Ala Gln His Leu Leu Gln Leu Thr Val Trp
            565                 570                 575

Gly Ile Lys Gln Leu Gln Ala Arg Ile Leu Ala Val Glu Arg Tyr Leu
            580                 585                 590

Lys Asp Gln Gln Leu Leu Gly Ile Trp Gly Cys Ser Gly Lys Leu Ile
            595                 600                 605

Cys Thr Thr Ala Val Pro Trp Asn Ala Ser Trp Ser Asn Lys Ser Leu
    610                 615                 620

Glu Gln Ile Trp Asn Asn Met Thr Trp Met Glu Trp Asp Arg Glu Ile
625                 630                 635                 640

Asn Asn Tyr Thr Ser Leu Ile His Ser Leu Ile Glu Glu Ser Gln Asn
            645                 650                 655

Gln Gln Glu Lys Asn Glu Gln Glu Leu Leu Glu Leu Asp Lys Trp Ala
            660                 665                 670

Ser Leu Trp Asn Trp Phe Asn Ile Thr Asn Trp Leu Trp Tyr Ile Lys
            675                 680                 685

Ile Phe Ile Met Ile Val Gly Gly Leu Val Gly Leu Arg Ile Val Phe
            690                 695                 700

Ala Val Leu Ser Ile Val Asn Arg Val Arg Gln Gly Tyr Ser Pro Leu
705                 710                 715                 720

Ser Phe Gln Thr His Leu Pro Thr Pro Arg Gly Pro Asp Arg Pro Glu
            725                 730                 735

Gly Ile Glu Glu Glu Gly Gly Glu Arg Asp Arg Asp Arg Ser Ile Arg
            740                 745                 750

Leu Val Asn Gly Ser Leu Ala Leu Ile Trp Asp Asp Leu Arg Ser Leu
            755                 760                 765

Cys Leu Phe Ser Tyr His Arg Leu Arg Asp Leu Leu Leu Ile Val Thr
```

```
                    770                 775                 780
Arg Ile Val Glu Leu Leu Gly Arg Arg Gly Trp Glu Ala Leu Lys Tyr
785                 790                 795                 800

Trp Trp Asn Leu Leu Gln Tyr Trp Ser Gln Glu Leu Lys Asn Ser Ala
                    805                 810                 815

Val Ser Leu Leu Asn Ala Thr Ala Ile Ala Val Ala Glu Gly Thr Asp
                    820                 825                 830

Arg Val Ile Glu Val Val Gln Gly Ala Cys Arg Ala Ile Arg His Ile
                    835                 840                 845

Pro Arg Arg Ile Arg Gln Gly Leu Glu Arg Ile Leu Leu
                    850                 855            860

(2) INFORMATION FOR SEQ ID NO:11:

(i) SEQUENCE CHARACTERISTICS:
        (A) LENGTH: 856 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

Met Arg Val Lys Gly Ile Arg Arg Asn Tyr Gln His Trp Trp Gly Trp
1               5                   10                  15

Gly Thr Met Leu Leu Gly Leu Leu Met Ile Cys Ser Ala Thr Glu Lys
                20                  25                  30

Leu Trp Val Thr Val Tyr Tyr Gly Val Pro Val Trp Lys Glu Ala Thr
                35                  40                  45

Thr Thr Leu Phe Cys Ala Ser Asp Ala Lys Ala Tyr Asp Thr Glu Val
50                  55                  60

His Asn Val Trp Ala Thr Gln Ala Cys Val Pro Thr Asp Pro Asn Pro
65                  70                  75                  80

Gln Glu Val Glu Leu Val Asn Val Thr Glu Asn Phe Asn Met Trp Lys
                85                  90                  95

Asn Asn Met Val Glu Gln Met His Glu Asp Ile Ile Ser Leu Trp Asp
                100                 105                 110

Gln Ser Leu Lys Pro Cys Val Lys Leu Thr Pro Leu Cys Val Thr Leu
                115                 120                 125

Asn Cys Thr Asp Leu Arg Asn Thr Thr Asn Thr Asn Asn Ser Thr Ala
130                 135                 140

Asn Asn Asn Ser Asn Ser Glu Gly Thr Ile Lys Gly Gly Glu Met Lys
145                 150                 155                 160

Asn Cys Ser Phe Asn Ile Thr Thr Ser Ile Arg Asp Lys Met Gln Lys
                165                 170                 175

Glu Tyr Ala Leu Leu Tyr Lys Leu Asp Ile Val Ser Ile Asp Asn Asp
                180                 185                 190

Ser Thr Ser Tyr Arg Leu Ile Ser Cys Asn Thr Ser Val Ile Thr Gln
                195                 200                 205

Ala Cys Pro Lys Ile Ser Phe Glu Pro Ile Pro Ile His Tyr Cys Ala
210                 215                 220

Pro Ala Gly Phe Ala Ile Leu Lys Cys Asn Asp Lys Lys Phe Ser Gly
225                 230                 235                 240

Lys Gly Ser Cys Lys Asn Val Ser Thr Val Gln Cys Thr His Gly Ile
                245                 250                 255

Arg Pro Val Val Ser Thr Gln Leu Leu Leu Asn Gly Ser Leu Ala Glu
```

-continued

```
                260                 265                 270
Glu Glu Val Val Ile Arg Ser Glu Asn Phe Thr Asp Asn Ala Lys Thr
                275                 280                 285

Ile Ile Val His Leu Asn Glu Ser Val Gln Ile Asn Cys Thr Arg Pro
            290                 295                 300

Asn Tyr Asn Lys Arg Lys Arg Ile His Ile Gly Pro Gly Arg Ala Phe
305                 310                 315                 320

Tyr Thr Thr Lys Asn Ile Ile Gly Thr Ile Arg Gln Ala His Cys Asn
                325                 330                 335

Ile Ser Arg Ala Lys Trp Asn Asp Thr Leu Arg Gln Ile Val Ser Lys
            340                 345                 350

Leu Lys Glu Gln Phe Lys Asn Lys Thr Ile Val Phe Asn Gln Ser Ser
                355                 360                 365

Gly Gly Asp Pro Glu Ile Val Met His Ser Phe Asn Cys Gly Gly Glu
            370                 375                 380

Phe Phe Tyr Cys Asn Thr Ser Pro Leu Phe Asn Ser Thr Trp Asn Gly
385                 390                 395                 400

Asn Asn Thr Trp Asn Asn Thr Thr Gly Ser Asn Asn Ile Thr Leu
                405                 410                 415

Gln Cys Lys Ile Lys Gln Ile Ile Asn Met Trp Gln Glu Val Gly Lys
            420                 425                 430

Ala Met Tyr Ala Pro Pro Ile Glu Gly Gln Ile Arg Cys Ser Ser Asn
            435                 440                 445

Ile Thr Gly Leu Leu Leu Thr Arg Asp Gly Gly Lys Asp Thr Asp Thr
            450                 455                 460

Asn Asp Thr Glu Ile Phe Arg Pro Gly Gly Gly Asp Met Arg Asp Asn
465                 470                 475                 480

Trp Arg Ser Glu Leu Tyr Lys Tyr Lys Val Val Thr Ile Glu Pro Leu
                485                 490                 495

Gly Val Ala Pro Thr Lys Ala Lys Arg Arg Val Val Gln Arg Glu Lys
            500                 505                 510

Arg Ala Ala Ile Gly Ala Leu Phe Leu Gly Phe Leu Gly Ala Ala Gly
            515                 520                 525

Ser Thr Met Gly Ala Ala Ser Val Thr Leu Thr Val Gln Ala Arg Leu
            530                 535                 540

Leu Leu Ser Gly Ile Val Gln Gln Asn Asn Leu Leu Arg Ala Ile
545                 550                 555                 560

Glu Ala Gln Gln His Met Leu Gln Leu Thr Val Trp Gly Ile Lys Gln
                565                 570                 575

Leu Gln Ala Arg Val Leu Ala Val Glu Arg Tyr Leu Lys Asp Gln Gln
            580                 585                 590

Leu Leu Gly Phe Trp Gly Cys Ser Gly Lys Leu Ile Cys Thr Thr Thr
            595                 600                 605

Val Pro Trp Asn Ala Ser Trp Ser Asn Lys Ser Leu Asp Asp Ile Trp
            610                 615                 620

Asn Asn Met Thr Trp Met Gln Trp Glu Arg Glu Ile Asp Asn Tyr Thr
625                 630                 635                 640

Ser Leu Ile Tyr Ser Leu Leu Glu Lys Ser Gln Thr Gln Gln Glu Lys
                645                 650                 655

Asn Glu Gln Glu Leu Leu Glu Leu Asp Lys Trp Ala Ser Leu Trp Asn
                660                 665                 670

Trp Phe Asp Ile Thr Asn Trp Leu Trp Tyr Ile Lys Ile Phe Ile Met
            675                 680                 685
```

```
Ile Val Gly Gly Leu Val Gly Leu Arg Ile Val Phe Ala Val Leu Ser
    690                 695                 700
Ile Val Asn Arg Val Arg Gln Gly Tyr Ser Pro Leu Ser Leu Gln Thr
705                 710                 715                 720
Arg Pro Pro Val Pro Arg Gly Pro Asp Arg Pro Glu Gly Ile Glu Glu
                725                 730                 735
Glu Gly Gly Glu Arg Asp Arg Asp Thr Ser Gly Arg Leu Val His Gly
                740                 745                 750
Phe Leu Ala Ile Ile Trp Val Asp Leu Arg Ser Leu Phe Leu Phe Ser
                755                 760                 765
Tyr His His Arg Asp Leu Leu Leu Ile Ala Ala Arg Ile Val Glu Leu
    770                 775                 780
Leu Gly Arg Arg Gly Trp Glu Val Leu Lys Tyr Trp Trp Asn Leu Leu
785                 790                 795                 800
Gln Tyr Trp Ser Gln Glu Leu Lys Ser Ser Ala Val Ser Leu Leu Asn
                805                 810                 815
Ala Thr Ala Ile Ala Val Ala Glu Gly Thr Asp Arg Val Ile Glu Val
                820                 825                 830
Leu Gln Arg Ala Gly Arg Ala Ile Leu His Ile Pro Thr Arg Ile Arg
                835                 840                 845
Gln Gly Leu Glu Arg Ala Leu Leu
    850                 855

(2) INFORMATION FOR SEQ ID NO:12:

(i) SEQUENCE CHARACTERISTICS:
        (A) LENGTH: 872 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

Met Arg Ala Arg Gly Ile Glu Arg Asn Cys Gln Asn Trp Trp Lys Trp
1               5                   10                  15
Gly Ile Met Leu Leu Gly Ile Leu Met Thr Cys Ser Ala Ala Asp Asn
                20                  25                  30
Leu Trp Val Thr Val Tyr Tyr Gly Val Pro Val Trp Lys Glu Ala Thr
                35                  40                  45
Thr Thr Leu Phe Cys Ala Ser Asp Ala Lys Ser Tyr Glu Thr Glu Ala
    50                  55                  60
His Asn Ile Trp Ala Thr His Ala Cys Val Pro Thr Asp Pro Asn Pro
65                  70                  75                  80
Gln Glu Ile Ala Leu Glu Asn Val Thr Glu Asn Phe Asn Met Trp Lys
                85                  90                  95
Asn Asn Met Val Glu Gln Met His Glu Asp Ile Ile Ser Leu Trp Asp
                100                 105                 110
Gln Ser Leu Lys Pro Cys Val Lys Leu Thr Pro Leu Cys Val Thr Leu
                115                 120                 125
Asn Cys Ser Asp Glu Leu Arg Asn Asn Gly Thr Met Gly Asn Asn Val
    130                 135                 140
Thr Thr Glu Glu Lys Gly Met Lys Asn Cys Ser Phe Asn Val Thr Thr
145                 150                 155                 160
Val Leu Lys Asp Lys Lys Gln Gln Val Tyr Ala Leu Phe Tyr Arg Leu
                165                 170                 175
```

```
Asp Ile Val Pro Ile Asp Asn Asp Ser Ser Thr Asn Ser Thr Asn Tyr
            180                 185                 190
Arg Leu Ile Asn Cys Asn Thr Ser Ala Ile Thr Gln Ala Cys Pro Lys
        195                 200                 205
Val Ser Phe Glu Pro Ile Pro Ile His Tyr Cys Ala Pro Ala Gly Phe
    210                 215                 220
Ala Ile Leu Lys Cys Arg Asp Lys Lys Phe Asn Gly Thr Gly Pro Cys
225                 230                 235                 240
Thr Asn Val Ser Thr Val Gln Cys Thr His Gly Ile Arg Pro Val Val
                245                 250                 255
Ser Thr Gln Leu Leu Leu Asn Gly Ser Leu Ala Glu Glu Val Ile
            260                 265                 270
Ile Arg Ser Glu Asn Leu Thr Asn Asn Ala Lys Asn Ile Ile Ala His
        275                 280                 285
Leu Asn Glu Ser Val Lys Ile Thr Cys Ala Arg Pro Tyr Gln Asn Thr
    290                 295                 300
Arg Gln Arg Thr Pro Ile Gly Leu Gly Gln Ser Leu Tyr Thr Thr Arg
305                 310                 315                 320
Ser Arg Ser Ile Ile Gly Gln Ala His Cys Asn Ile Ser Arg Ala Gln
                325                 330                 335
Trp Ser Lys Thr Leu Gln Gln Val Ala Arg Lys Leu Gly Thr Leu Leu
            340                 345                 350
Asn Lys Thr Ile Ile Lys Phe Lys Pro Ser Ser Gly Gly Asp Pro Glu
        355                 360                 365
Ile Thr Thr His Ser Phe Asn Cys Gly Gly Glu Phe Phe Tyr Cys Asn
    370                 375                 380
Thr Ser Gly Leu Phe Asn Ser Thr Trp Asn Ile Ser Ala Trp Asn Asn
385                 390                 395                 400
Ile Thr Glu Ser Asn Asn Ser Thr Asn Thr Asn Ile Thr Leu Gln Cys
                405                 410                 415
Arg Ile Lys Gln Ile Ile Lys Met Val Ala Gly Arg Lys Ala Ile Tyr
            420                 425                 430
Ala Pro Pro Ile Glu Arg Asn Ile Leu Cys Ser Ser Asn Ile Thr Gly
        435                 440                 445
Leu Leu Leu Thr Arg Asp Gly Gly Ile Asn Asn Ser Thr Asn Glu Thr
    450                 455                 460
Phe Arg Pro Gly Gly Gly Asp Met Arg Asp Asn Trp Arg Ser Glu Leu
465                 470                 475                 480
Tyr Lys Tyr Lys Val Val Gln Ile Glu Pro Leu Gly Val Ala Pro Thr
                485                 490                 495
Arg Ala Lys Arg Arg Val Val Glu Arg Glu Lys Arg Ala Ile Gly Leu
            500                 505                 510
Gly Ala Met Phe Leu Gly Phe Leu Gly Ala Ala Gly Ser Thr Met Gly
        515                 520                 525
Ala Arg Ser Val Thr Leu Thr Val Gln Ala Arg Gln Leu Met Ser Gly
    530                 535                 540
Ile Val Gln Gln Gln Asn Asn Leu Leu Arg Ala Ile Glu Ala Gln Gln
545                 550                 555                 560
His Leu Leu Gln Leu Thr Val Trp Gly Ile Lys Gln Leu Gln Ala Arg
                565                 570                 575
Ile Leu Ala Val Glu Arg Tyr Leu Lys Asp Gln Gln Leu Leu Gly Ile
            580                 585                 590
```

```
Trp Gly Cys Ser Gly Lys His Ile Cys Thr Thr Asn Val Pro Trp Asn
        595                 600                 605

Ser Ser Trp Ser Asn Arg Ser Leu Asn Glu Ile Trp Gln Asn Met Thr
    610                 615                 620

Trp Met Glu Trp Glu Arg Glu Ile Asp Asn Tyr Thr Gly Leu Ile Tyr
625                 630                 635                 640

Ser Leu Ile Glu Glu Ser Gln Thr Gln Gln Glu Lys Asn Glu Lys Glu
                645                 650                 655

Leu Leu Glu Leu Asp Lys Trp Ala Ser Leu Trp Asn Trp Phe Ser Ile
            660                 665                 670

Thr Gln Trp Leu Trp Tyr Ile Lys Ile Phe Ile Met Ile Ile Gly Gly
            675                 680                 685

Leu Ile Gly Leu Arg Ile Val Phe Ala Val Leu Ser Leu Val Asn Arg
        690                 695                 700

Val Arg Gln Gly Tyr Ser Pro Leu Ser Phe Gln Thr Leu Leu Pro Ala
705                 710                 715                 720

Pro Arg Gly Pro Asp Arg Pro Glu Gly Thr Glu Glu Glu Gly Gly Glu
                725                 730                 735

Arg Gly Arg Asp Arg Ser Val Arg Leu Leu Asn Gly Phe Ser Ala Leu
            740                 745                 750

Ile Trp Asp Asp Leu Arg Ser Leu Cys Leu Phe Ser Tyr His Arg Leu
        755                 760                 765

Arg Asp Leu Ile Leu Ile Ala Val Arg Ile Val Glu Leu Leu Gly Arg
770                 775                 780

Arg Gly Trp Asp Ile Leu Lys Tyr Leu Trp Asn Leu Leu Gln Tyr Trp
785                 790                 795                 800

Ser Gln Glu Leu Arg Asn Ser Ala Ser Ser Leu Phe Asp Ala Ile Ala
                805                 810                 815

Ile Ala Val Ala Glu Gly Thr Asp Arg Val Ile Glu Ile Ile Gln Arg
            820                 825                 830

Ala Cys Arg Ala Val Leu Asn Ile Pro Arg Arg Ile Arg Gln Gly Leu
        835                 840                 845

Glu Arg Ser Leu Leu Asn Gly Trp Gln Met Val Lys Lys Tyr Ser Gly
    850                 855                 860

Met Ala Cys Tyr Lys Gly Lys Asn
865                 870

(2) INFORMATION FOR SEQ ID NO:13:

(i) SEQUENCE CHARACTERISTICS:
        (A) LENGTH: 865 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

Met Arg Val Met Glu Met Arg Lys Asn Cys Gln His Leu Trp Lys Trp
1               5                   10                  15

Gly Thr Met Leu Leu Gly Met Leu Met Ile Cys Ser Ala Ala Glu Asp
            20                  25                  30

Leu Trp Val Thr Val Tyr Tyr Gly Val Pro Val Trp Lys Glu Ala Thr
        35                  40                  45

Thr Thr Leu Phe Cys Ala Ser Glu Ala Lys Ala Tyr Lys Thr Glu Val
    50                  55                  60
```

-continued

```
His Asn Val Trp Ala Lys His Ala Cys Val Pro Thr Asp Pro Asn Pro
 65                  70                  75                  80

Gln Glu Val Leu Leu Glu Asn Val Thr Glu Asn Phe Asn Met Trp Lys
                 85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Ala Asn Leu Asn Gly Thr Asn Val Thr Ser Ser Ser
    130                 135                 140

Gly Gly Thr Met Met Glu Asn Gly Glu Ile Lys Asn Cys Ser Phe Gln
145                 150                 155                 160

Val Thr Thr Ser Arg Arg Asp Lys Thr Gln Lys Lys Tyr Ala Leu Phe
                165                 170                 175

Tyr Lys Leu Asp Val Val Pro Ile Glu Lys Gly Asn Ile Ser Pro Lys
            180                 185                 190

Asn Asn Thr Ser Asn Asn Thr Ser Tyr Gly Asn Tyr Thr Leu Ile His
        195                 200                 205

Cys Asn Ser Ser Val Ile Thr Gln Ala Cys Pro Lys Val Ser Phe Glu
    210                 215                 220

Pro Ile Pro Ile His Tyr Cys Thr Pro Ala Gly Phe Ala Ile Leu Lys
225                 230                 235                 240

Cys Asn Asp Lys Lys Phe Asn Gly Thr Gly Pro Cys Lys Asn Val Ser
                245                 250                 255

Thr Val Gln Cys Thr His Gly Ile Arg Pro Val Val Ser Thr Gln Leu
            260                 265                 270

Leu Leu Asn Gly Ser Leu Ala Glu Glu Val Val Ile Arg Ser Glu
        275                 280                 285

Asn Phe Thr Asp Asn Val Lys Thr Ile Ile Val Gln Leu Asn Ala Ser
    290                 295                 300

Val Gln Ile Asn Cys Thr Arg Pro Asn Asn Thr Arg Lys Ser Ile
305                 310                 315                 320

Thr Lys Gly Pro Gly Arg Val Ile Tyr Ala Thr Gly Gln Ile Ile Gly
                325                 330                 335

Asp Ile Arg Lys Ala His Cys Asn Leu Ser Arg Ala Gln Trp Asn Asn
            340                 345                 350

Thr Leu Lys Gln Val Val Thr Lys Leu Arg Glu Gln Phe Asp Asn Lys
        355                 360                 365

Thr Ile Val Phe Thr Ser Ser Gly Gly Asp Pro Glu Ile Val Leu
    370                 375                 380

His Ser Phe Asn Cys Gly Gly Glu Phe Phe Tyr Cys Asn Thr Thr Gln
385                 390                 395                 400

Leu Phe Asn Ser Thr Trp Asn Ser Thr Glu Gly Ser Asn Asn Thr Gly
                405                 410                 415

Gly Asn Asp Thr Ile Thr Leu Pro Cys Arg Ile Lys Gln Ile Val Asn
            420                 425                 430

Met Trp Gln Glu Val Gly Lys Ala Met Tyr Ala Pro Pro Ile Ser Gly
        435                 440                 445

Gln Ile Lys Cys Ile Ser Asn Ile Thr Gly Leu Leu Leu Thr Arg Asp
    450                 455                 460

Gly Gly Glu Asp Thr Thr Asn Thr Thr Glu Ile Phe Arg Leu Gly Gly
465                 470                 475                 480

Gly Asn Met Arg Asp Asn Trp Arg Ser Glu Leu Tyr Lys Tyr Lys Val
```

-continued

```
                485                 490                 495
Val Arg Ile Glu Pro Leu Gly Val Ala Pro Thr Arg Ala Lys Arg Arg
            500                 505                 510
Val Val Gln Arg Glu Lys Arg Ala Val Gly Thr Ile Gly Ala Met Phe
        515                 520                 525
Leu Gly Phe Leu Gly Ala Ala Gly Ser Thr Met Gly Ala Gly Ser Ile
    530                 535                 540
Thr Leu Thr Val Gln Ala Arg His Leu Leu Ser Gly Ile Val Gln Gln
545                 550                 555                 560
Gln Asn Asn Leu Leu Arg Ala Ile Glu Ala Gln Gln His Leu Leu Gln
                565                 570                 575
Leu Thr Val Trp Gly Ile Lys Gln Leu Gln Ala Arg Val Leu Ala Val
            580                 585                 590
Glu Arg Tyr Leu Arg Asp Gln Gln Leu Leu Gly Ile Trp Gly Cys Ser
        595                 600                 605
Gly Lys Leu Ile Cys Thr Thr Thr Val Pro Trp Asn Ala Ser Trp Ser
    610                 615                 620
Asn Lys Ser Leu Asn Met Ile Trp Asn Asn Met Thr Trp Met Gln Trp
625                 630                 635                 640
Glu Arg Glu Ile Asp Asn Tyr Thr Gly Ile Ile Tyr Asn Leu Leu Glu
                645                 650                 655
Glu Ser Gln Asn Gln Gln Glu Lys Asn Glu Gln Glu Leu Leu Glu Leu
            660                 665                 670
Asp Lys Trp Ala Asn Leu Trp Asn Trp Phe Asp Ile Thr Gln Trp Leu
        675                 680                 685
Trp Tyr Ile Arg Ile Phe Ile Met Ile Val Gly Gly Leu Val Gly Leu
    690                 695                 700
Lys Ile Val Phe Ala Val Leu Ser Ile Val Asn Arg Val Arg Gln Gly
705                 710                 715                 720
Tyr Ser Pro Leu Ser Phe Gln Thr His Leu Pro Ala Pro Arg Gly Pro
                725                 730                 735
Asp Arg Pro Glu Gly Ile Glu Gly Gly Gly Glu Arg Asp Arg Asp
            740                 745                 750
Arg Ser Gly Gly Ala Val Asn Gly Phe Leu Thr Leu Ile Trp Asp Asp
        755                 760                 765
Leu Trp Thr Leu Cys Ser Phe Ser Tyr His Arg Leu Arg Asp Leu Leu
    770                 775                 780
Leu Ile Val Val Arg Ile Val Glu Leu Leu Gly Arg Arg Gly Trp Glu
785                 790                 795                 800
Ala Leu Lys Tyr Trp Trp Asn Leu Leu Gln Tyr Trp Ser Gln Glu Leu
                805                 810                 815
Lys Asn Ser Ala Val Ser Leu Leu Asn Thr Thr Ala Ile Ala Val Ala
            820                 825                 830
Glu Gly Thr Asp Arg Ile Ile Glu Val Ala Gln Arg Ile Leu Arg Ala
        835                 840                 845
Phe Leu His Ile Pro Arg Arg Ile Arg Gln Gly Leu Glu Arg Ala Leu
    850                 855                 860
Leu
865
```

(2) INFORMATION FOR SEQ ID NO:14:

(i) SEQUENCE CHARACTERISTICS:
        (A) LENGTH: 855 amino acids (B) TYPE: amino acid
(C) STRANDEDNESS: single
(D) TOPOLOGY: linear (ii) MOLECULE TYPE: DNA (genomic)

(xi) SEQUENCE DESCRIPTION: SEQ ID NO:14:

```
Met Arg Val Lys Gly Ser Gly Arg Asn Tyr Gln His Leu Trp Arg Trp
1               5                   10                  15

Gly Thr Met Leu Leu Gly Ile Leu Met Ile Cys Ser Ala Ala Glu Gln
            20                  25                  30

Leu Trp Val Thr Val Tyr Tyr Gly Val Pro Val Trp Lys Glu Ala Thr
                35                  40                  45

Thr Thr Leu Phe Cys Ala Ser Asp Ala Lys Ala Tyr Asp Thr Glu Val
50                  55                  60

His Asn Ile Trp Ala Thr His Ala Cys Val Pro Thr Asp Pro Asn Pro
65                  70                  75                  80

Gln Glu Val Val Leu Gly Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asn Leu Arg Asn Asp Thr Ser Thr Asn Ala Thr Asn Thr
130                 135                 140

Thr Ser Ser Asn Arg Gly Lys Met Glu Gly Gly Glu Met Thr Asn Cys
145                 150                 155                 160

Ser Phe Asn Ile Thr Thr Ser Ile Arg Ser Lys Val Gln Lys Glu Tyr
                165                 170                 175

Ala Leu Phe Tyr Lys Leu Asp Val Val Pro Ile Asp Asn Thr Ser Tyr
            180                 185                 190

Thr Leu Ile Asn Cys Asn Thr Ser Val Ile Thr Gln Ala Cys Pro Lys
        195                 200                 205

Val Ser Phe Glu Pro Ile Pro Ile His Tyr Cys Ala Arg Trp Phe Ala
210                 215                 220

Ile Leu Asn Cys Asn Asn Lys Lys Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr His Leu Leu Leu Asn Gly Ser Leu Ala Glu Glu Val Val Leu
            260                 265                 270

Arg Ser Glu Asn Phe Thr Asp Asn Ala Lys Thr Ile Ile Val Gln Leu
        275                 280                 285

Lys Glu Ala Val Glu Ile Asn Cys Thr Arg Pro Asn Asn Asn Thr Thr
290                 295                 300

Arg Ser Ile His Ile Gly Pro Gly Arg Ala Phe Tyr Ala Thr Gly Asp
305                 310                 315                 320

Ile Ile Gly Asp Ile Arg Gln Ala His Cys Asn Ile Ser Arg Ala Lys
                325                 330                 335

Trp Asn Asn Thr Leu Lys Gln Ile Val Ile Lys Leu Arg Asp Gln Phe
            340                 345                 350

Glu Asn Lys Thr Ile Ile Phe Asn Arg Ser Ser Gly Gly Asp Pro Glu
        355                 360                 365

Ile Val Met His Ser Phe Asn Cys Gly Gly Glu Phe Phe Tyr Cys Asn
370                 375                 380
```

```
Ser Thr Gln Leu Phe Ser Ser Thr Trp Asn Gly Thr Glu Gly Ser Asn
385                 390                 395                 400

Asn Thr Gly Gly Asn Asp Thr Ile Thr Leu Pro Cys Arg Ile Lys Glu
        405                 410                 415

Ile Ile Asn Met Trp Gln Glu Val Gly Lys Ala Met Tyr Ala Pro Pro
            420                 425                 430

Ile Lys Gly Gln Val Lys Cys Ser Ser Asn Ile Thr Gly Leu Leu Leu
        435                 440                 445

Thr Arg Asp Gly Asn Ser Lys Asn Gly Ser Lys Asn Glu Asn Thr
450                 455                 460

Glu Ile Phe Arg Pro Gly Gly Asp Met Arg Asp Asn Trp Arg Ser
465                 470                 475                 480

Glu Leu Tyr Lys Tyr Lys Val Val Lys Ile Glu Pro Leu Gly Val Ala
                485                 490                 495

Pro Thr Lys Ala Lys Arg Val Gln Arg Glu Lys Arg Ala Val
            500                 505                 510

Gly Thr Ile Gly Ala Met Phe Leu Gly Phe Leu Gly Ala Ala Gly Ser
            515                 520                 525

Thr Met Gly Ala Thr Ser Met Thr Leu Thr Val Gln Ala Arg Leu Leu
530                 535                 540

Leu Ser Gly Ile Val Gln Gln Gln Asn Asn Leu Leu Arg Ala Ile Glu
545                 550                 555                 560

Ala Gln Gln His Leu Leu Gln Leu Thr Val Trp Gly Ile Lys Gln Leu
                565                 570                 575

Gln Ala Arg Val Leu Ala Val Glu Arg Tyr Leu Arg Asp Gln Gln Leu
            580                 585                 590

Leu Gly Ile Trp Gly Cys Ser Gly Lys Leu Ile Cys Thr Thr Thr Val
        595                 600                 605

Pro Trp Asn Thr Ser Trp Ser Asn Lys Ser Leu Asp Lys Ile Trp Gly
610                 615                 620

Asn Met Thr Trp Met Glu Trp Glu Arg Glu Ile Asp Asn Tyr Thr Ser
625                 630                 635                 640

Leu Ile Tyr Thr Leu Ile Glu Glu Ser Gln Asn Gln Gln Glu Lys Asn
                645                 650                 655

Glu Gln Glu Leu Leu Glu Leu Asp Lys Trp Ala Ser Leu Trp Asn Trp
            660                 665                 670

Phe Asn Ile Thr Asn Trp Leu Trp Tyr Ile Lys Ile Phe Ile Met Ile
        675                 680                 685

Val Gly Gly Leu Val Gly Leu Arg Ile Val Phe Thr Val Leu Ser Ile
690                 695                 700

Val Asn Arg Val Arg Gln Gly Tyr Ser Pro Leu Ser Phe Gln Thr Arg
705                 710                 715                 720

Leu Pro Ser Gln Arg Gly Pro Asp Arg Pro Glu Gly Ile Glu Glu Glu
                725                 730                 735

Gly Gly Glu Arg Asp Arg Asp Arg Ser Gly Arg Leu Val Asp Gly Phe
            740                 745                 750

Leu Ala Ile Ile Trp Val Asp Arg Ser Leu Cys Leu Phe Ser Tyr His
            755                 760                 765

Arg Leu Arg Asp Leu Leu Leu Ile Val Thr Arg Ile Val Glu Leu Leu
        770                 775                 780

Gly Arg Arg Gly Trp Glu Ala Leu Lys Tyr Trp Trp Asn Leu Leu Gln
785                 790                 795                 800
```

```
Tyr Trp Ser Gln Glu Leu Arg Asn Ser Ala Val Ser Phe Val Asn Ala
                805                 810                 815

Thr Ala Ile Ala Val Ala Glu Gly Thr Asp Arg Val Ile Glu Leu Leu
            820                 825                 830

Gln Arg Ala Phe Arg Ala Ile Leu His Ile Pro Thr Arg Ile Arg Gln
        835                 840                 845

Gly Leu Glu Arg Ala Leu Gln
    850                 855

(2) INFORMATION FOR SEQ ID NO:15:

(i) SEQUENCE CHARACTERISTICS:
        (A) LENGTH: 855 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

Met Lys Val Lys Gly Thr Arg Arg Asn Tyr Gln His Leu Trp Arg Trp
1               5                   10                  15

Gly Thr Leu Leu Leu Gly Met Leu Met Ile Cys Ser Ala Thr Glu Lys
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Arg Ala Tyr Asp Thr Glu Val
    50                  55                  60

His Asn Val Trp Ala Thr His Ala Cys Val Pro Thr Asp Pro Asn Pro
65                  70                  75                  80

Gln Glu Val Val Leu Gly Asn Val Thr Glu Asn Phe Asn Met Trp Lys
                85                  90                  95

Asn Asn Met Val Glu Gln Met Gln Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Leu Gly Lys Ala Thr Asn Thr Asn Ser Ser Asn Trp
    130                 135                 140

Lys Glu Glu Ile Lys Gly Glu Ile Lys Asn Cys Ser Phe Asn Ile Thr
145                 150                 155                 160

Thr Ser Ile Arg Asp Lys Ile Gln Lys Glu Asn Ala Leu Phe Arg Asn
                165                 170                 175

Leu Asp Val Val Pro Ile Asp Asn Ala Ser Thr Thr Thr Asn Tyr Thr
            180                 185                 190

Asn Tyr Arg Leu Ile His Cys Asn Arg Ser Val Ile Thr Gln Ala Cys
        195                 200                 205

Pro Lys Val Ser Phe Glu Pro Ile Pro Ile His Tyr Cys Thr Pro Ala
    210                 215                 220

Gly Phe Ala Ile Leu Lys Cys Asn Asn Lys Thr Phe Asn Gly Lys Gly
225                 230                 235                 240

Thr Cys Thr Asn Val Ser Thr Val Gln Cys Thr His Gly Ile Arg Pro
                245                 250                 255

Ile Val Ser Thr Gln Leu Leu Leu Asn Gly Ser Leu Ala Glu Glu Glu
            260                 265                 270

Val Val Ile Arg Ser Asp Asn Phe Thr Asn Asn Ala Lys Thr Ile Ile
        275                 280                 285
```

```
Val Gln Leu Asn Glu Ser Val Ala Ile Asn Cys Thr Arg Pro Asn Asn
    290                 295                 300

Asn Thr Arg Lys Ser Ile Tyr Ile Gly Pro Gly Arg Ala Phe His Thr
305                 310                 315                 320

Thr Gly Arg Ile Ile Gly Asp Ile Arg Lys Ala His Cys Asn Ile Ser
                325                 330                 335

Arg Ala Gln Trp Asn Asn Thr Leu Glu Gln Ile Val Lys Lys Leu Arg
            340                 345                 350

Glu Gln Phe Gly Asn Asn Lys Thr Ile Val Phe Asn Gln Ser Ser Gly
        355                 360                 365

Gly Asp Pro Glu Ile Val Met His Ser Phe Asn Cys Arg Gly Glu Phe
    370                 375                 380

Phe Tyr Cys Asn Thr Thr Gln Leu Phe Asn Asn Thr Trp Arg Leu Asn
385                 390                 395                 400

His Thr Glu Gly Thr Lys Gly Asn Asp Thr Ile Ile Leu Pro Cys Arg
                405                 410                 415

Ile Lys Gln Ile Ile Asn Met Trp Gln Glu Val Gly Lys Ala Met Tyr
            420                 425                 430

Ala Pro Pro Ile Gly Gly Gln Ile Ser Cys Ser Ser Asn Ile Thr Gly
        435                 440                 445

Leu Leu Leu Thr Arg Asp Gly Gly Thr Asn Val Thr Asn Asp Thr Glu
    450                 455                 460

Val Phe Arg Pro Gly Gly Gly Asp Met Arg Asp Asn Trp Arg Ser Glu
465                 470                 475                 480

Leu Tyr Lys Tyr Lys Val Ile Lys Ile Glu Pro Leu Gly Ile Ala Pro
                485                 490                 495

Thr Lys Ala Lys Arg Arg Val Val Gln Arg Glu Lys Arg Ala Val Gly
            500                 505                 510

Ile Val Gly Ala Met Phe Leu Gly Phe Leu Gly Ala Ala Gly Ser Thr
        515                 520                 525

Met Gly Ala Val Ser Leu Thr Leu Thr Val Gln Ala Arg Gln Leu Leu
    530                 535                 540

Ser Gly Ile Val Gln Gln Gln Asn Asn Leu Leu Arg Ala Ile Glu Ala
545                 550                 555                 560

Gln Gln His Leu Leu Gln Leu Thr Val Trp Gly Ile Lys Gln Leu Gln
                565                 570                 575

Ala Arg Val Leu Ala Val Glu Arg Tyr Leu Arg Asp Gln Gln Leu Leu
            580                 585                 590

Gly Ile Trp Gly Cys Ser Gly Lys Leu Ile Cys Thr Thr Ala Val Pro
        595                 600                 605

Trp Asn Ala Ser Trp Ser Asn Lys Ser Leu Glu Asp Ile Trp Asp Asn
    610                 615                 620

Met Thr Trp Met Gln Trp Glu Arg Glu Ile Asp Asn Tyr Thr Asn Thr
625                 630                 635                 640

Ile Tyr Thr Leu Leu Glu Glu Ser Gln Asn Gln Gln Glu Lys Asn Glu
                645                 650                 655

Gln Glu Leu Leu Glu Leu Asp Lys Trp Ala Ser Leu Trp Asn Trp Phe
            660                 665                 670

Ser Ile Thr Asn Trp Leu Trp Tyr Ile Lys Ile Phe Ile Met Ile Val
        675                 680                 685

Gly Gly Leu Val Gly Leu Arg Ile Val Phe Ala Val Leu Ser Ile Val
    690                 695                 700

Asn Arg Val Arg Gln Gly Tyr Ser Pro Leu Ser Phe Gln Thr Arg Leu
```

```
                    705                  710                  715                  720
Pro Val Pro Arg Gly Pro Asp Arg Pro Asp Gly Ile Glu Glu Gly
                725                  730                  735

Gly Glu Arg Asp Arg Asp Arg Ser Val Arg Leu Val Asp Gly Phe Leu
                740                  745                  750

Ala Leu Ile Trp Glu Asp Leu Arg Ser Leu Cys Leu Phe Ser Tyr Arg
                755                  760                  765

Arg Leu Arg Asp Leu Leu Leu Ile Ala Ala Arg Thr Val Glu Ile Leu
                770                  775                  780

Gly His Arg Gly Trp Glu Ala Leu Lys Tyr Trp Trp Ser Leu Leu Gln
785                  790                  795                  800

Tyr Trp Ile Gln Glu Leu Lys Asn Ser Ala Val Ser Trp Leu Asn Ala
                805                  810                  815

Thr Ala Ile Ala Val Thr Glu Gly Thr Asp Arg Val Ile Glu Val Ala
                820                  825                  830

Gln Arg Ala Tyr Arg Ala Ile Leu His Ile His Arg Ile Arg Gln
                835                  840                  845

Gly Leu Glu Arg Leu Leu Leu
    850                  855
```

(2) INFORMATION FOR SEQ ID NO:16:

(i) SEQUENCE CHARACTERISTICS:
        (A) LENGTH: 861 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

```
Met Arg Val Lys Glu Lys Tyr Gln His Leu Trp Arg Trp Gly Trp Lys
1                   5                  10                  15

Trp Gly Thr Met Leu Leu Gly Ile Leu Met Ile Cys Ser Ala Thr Glu
                20                  25                  30

Lys Leu Trp Val Thr Val Tyr Tyr Gly Val Pro Val Trp Lys Glu Ala
            35                  40                  45

Thr Thr Thr Leu Phe Cys Ala Ser Asp Ala Lys Ala Tyr Asp Thr Glu
50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
                100                 105                 110

Asp Gln Ser Leu Lys Pro Cys Val Lys Leu Thr Pro Leu Cys Val Ser
            115                 120                 125

Leu Lys Cys Thr Asp Leu Gly Asn Ala Thr Asn Thr Asn Ser Ser Asn
130                 135                 140

Thr Asn Ser Ser Ser Gly Glu Met Met Met Glu Lys Gly Glu Ile Lys
145                 150                 155                 160

Asn Cys Ser Phe Asn Ile Ser Thr Ser Ile Arg Gly Lys Val Gln Lys
                165                 170                 175

Glu Tyr Ala Phe Phe Tyr Lys Leu Asp Ile Ile Pro Ile Asp Asn Asp
            180                 185                 190

Thr Thr Ser Tyr Thr Leu Thr Ser Cys Asn Thr Ser Val Ile Thr Gln
```

-continued

```
                195                 200                 205
    Ala Cys Pro Lys Val Ser Phe Glu Pro Ile Pro Ile His Tyr Cys Ala
        210                 215                 220
    Pro Ala Gly Phe Ala Ile Leu Phe Cys Asn Asn Lys Thr Phe Asn Gly
    225                 230                 235                 240
    Thr Gly Pro Cys Thr Asn Val Ser Thr Val Gln Cys Thr His Gly Ile
                    245                 250                 255
    Arg Pro Val Val Ser Thr Gln Leu Leu Leu Asn Gly Ser Leu Ala Glu
                260                 265                 270
    Glu Glu Val Val Ile Arg Ser Ala Asn Phe Thr Asp Asn Ala Lys Thr
                275                 280                 285
    Ile Ile Val Gln Leu Asn Gln Ser Val Glu Ile Asn Cys Thr Arg Pro
        290                 295                 300
    Asn Asn Asn Thr Arg Lys Ser Ile Arg Ile Gln Arg Gly Pro Gly Arg
    305                 310                 315                 320
    Ala Phe Val Thr Ile Gly Lys Ile Gly Asn Met Arg Gln Ala His Cys
                    325                 330                 335
    Asn Ile Ser Arg Ala Lys Trp Asn Ala Thr Leu Lys Gln Ile Ala Ser
                340                 345                 350
    Lys Leu Arg Glu Gln Phe Gly Asn Asn Lys Thr Ile Ile Phe Lys Gln
                355                 360                 365
    Ser Ser Gly Gly Asp Pro Glu Ile Val Thr His Ser Phe Asn Cys Gly
        370                 375                 380
    Gly Glu Phe Phe Tyr Cys Asn Ser Thr Gln Leu Phe Asn Ser Thr Trp
    385                 390                 395                 400
    Phe Asn Ser Thr Trp Ser Thr Glu Gly Ser Asn Asn Thr Glu Gly Ser
                    405                 410                 415
    Asp Thr Ile Thr Leu Pro Cys Arg Ile Lys Gln Phe Ile Asn Met Trp
                420                 425                 430
    Gln Glu Val Gly Lys Ala Met Tyr Ala Pro Pro Ile Ser Gly Gln Ile
                435                 440                 445
    Arg Cys Ser Ser Asn Ile Thr Gly Leu Leu Leu Thr Arg Asp Gly Gly
        450                 455                 460
    Asn Asn Asn Asn Gly Ser Glu Ile Phe Arg Pro Gly Gly Gly Asp Met
    465                 470                 475                 480
    Arg Asp Asn Trp Arg Ser Glu Leu Tyr Lys Tyr Lys Val Val Lys Ile
                    485                 490                 495
    Glu Pro Leu Gly Val Ala Pro Thr Lys Ala Lys Arg Arg Val Val Gln
                500                 505                 510
    Arg Glu Lys Arg Ala Val Gly Ile Gly Ala Leu Phe Leu Gly Phe Leu
                515                 520                 525
    Gly Ala Ala Gly Ser Thr Met Gly Ala Arg Ser Met Thr Leu Thr Val
        530                 535                 540
    Gln Ala Arg Gln Leu Leu Ser Gly Ile Val Gln Gln Gln Asn Asn Leu
    545                 550                 555                 560
    Leu Arg Ala Ile Glu Ala Gln Gln His Leu Leu Gln Leu Thr Val Trp
                    565                 570                 575
    Gly Ile Lys Gln Leu Gln Ala Arg Ile Leu Ala Val Glu Arg Tyr Leu
                580                 585                 590
    Lys Asp Gln Gln Leu Leu Gly Ile Trp Gly Cys Ser Gly Lys Leu Ile
                595                 600                 605
    Cys Thr Thr Ala Val Pro Trp Asn Ala Ser Trp Ser Asn Lys Ser Leu
        610                 615                 620
```

```
Glu Gln Ile Trp Asn Asn Met Thr Trp Met Glu Trp Asp Arg Glu Ile
625                 630                 635                 640

Asn Asn Tyr Thr Ser Leu Ile His Ser Leu Ile Glu Glu Ser Gln Asn
            645                 650                 655

Gln Gln Glu Lys Asn Glu Gln Glu Leu Leu Glu Leu Asp Lys Trp Ala
        660                 665                 670

Ser Leu Trp Asn Trp Phe Asn Ile Thr Asn Trp Leu Trp Tyr Ile Lys
    675                 680                 685

Ile Phe Ile Met Ile Val Gly Gly Leu Val Gly Leu Arg Ile Val Phe
690                 695                 700

Ala Val Leu Ser Ile Val Asn Arg Val Arg Gln Gly Tyr Ser Pro Leu
705                 710                 715                 720

Ser Phe Gln Thr His Leu Pro Thr Pro Arg Gly Pro Asp Arg Pro Glu
            725                 730                 735

Gly Ile Glu Glu Glu Gly Gly Glu Arg Asp Arg Asp Arg Ser Ile Arg
                740                 745                 750

Leu Val Asn Gly Ser Leu Ala Leu Ile Trp Asp Asp Leu Arg Ser Leu
            755                 760                 765

Cys Leu Phe Ser Tyr His Arg Leu Arg Asp Leu Leu Leu Ile Val Thr
770                 775                 780

Arg Ile Val Glu Leu Leu Gly Arg Arg Gly Trp Glu Ala Leu Lys Tyr
785                 790                 795                 800

Trp Trp Asn Leu Leu Gln Tyr Trp Ser Gln Glu Leu Lys Asn Ser Ala
                805                 810                 815

Val Ser Leu Leu Asn Ala Thr Ala Ile Ala Val Ala Glu Gly Thr Asp
            820                 825                 830

Arg Val Ile Glu Val Val Gln Gly Ala Cys Arg Ala Ile Arg His Ile
            835                 840                 845

Pro Arg Arg Ile Arg Gln Gly Leu Glu Arg Ile Leu Leu
850                 855                 860

(2) INFORMATION FOR SEQ ID NO:17:

(i) SEQUENCE CHARACTERISTICS:
        (A) LENGTH: 858 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

Met Met Asn Gln Leu Leu Ile Ala Ile Leu Leu Ala Ser Ala Cys Leu
1               5                   10                  15

Val Tyr Cys Thr Gln Tyr Val Thr Val Phe Tyr Gly Val Pro Thr Trp
                20                  25                  30

Lys Asn Ala Thr Ile Pro Leu Phe Cys Ala Thr Arg Asn Arg Asp Thr
            35                  40                  45

Trp Gly Thr Ile Gln Cys Leu Pro Asp Asn Asp Asp Tyr Gln Glu Ile
        50                  55                  60

Thr Leu Asn Val Thr Glu Ala Phe Asp Ala Trp Asn Asn Thr Val Thr
65                  70                  75                  80

Glu Gln Ala Ile Glu Asp Val Trp His Leu Phe Glu Thr Ser Ile Lys
                85                  90                  95

Pro Cys Val Lys Leu Thr Pro Leu Cys Val Ala Met Lys Cys Ser Ser
            100                 105                 110
```

-continued

```
Thr Glu Ser Ser Thr Gly Asn Asn Thr Thr Ser Lys Ser Thr Ser Thr
        115                 120                 125
Thr Thr Thr Thr Pro Thr Asp Gln Glu Gln Glu Ile Ser Glu Asp Thr
130                 135                 140
Pro Cys Ala Arg Ala Asp Asn Cys Ser Gly Leu Gly Glu Glu Glu Thr
145                 150                 155                 160
Ile Asn Cys Gln Phe Asn Met Thr Gly Leu Glu Arg Asp Lys Lys Lys
                165                 170                 175
Gln Tyr Asn Glu Thr Trp Tyr Ser Lys Asp Val Val Cys Glu Thr Asn
            180                 185                 190
Asn Ser Thr Asn Gln Thr Gln Cys Tyr Met Asn His Cys Asn Thr Ser
        195                 200                 205
Val Ile Thr Glu Ser Cys Asp Lys His Tyr Trp Asp Ala Ile Arg Phe
    210                 215                 220
Arg Tyr Cys Ala Pro Pro Gly Tyr Ala Leu Leu Arg Cys Asn Asp Thr
225                 230                 235                 240
Asn Tyr Ser Gly Phe Ala Pro Asn Cys Ser Lys Val Val Ala Ser Thr
                245                 250                 255
Cys Thr Arg Met Met Glu Thr Gln Thr Ser Thr Trp Phe Gly Phe Asn
            260                 265                 270
Gly Thr Arg Ala Glu Asn Arg Thr Tyr Ile Tyr Trp His Gly Arg Asp
        275                 280                 285
Asn Arg Thr Ile Ile Ser Leu Asn Lys Tyr Tyr Asn Leu Ser Leu His
    290                 295                 300
Cys Lys Arg Pro Gly Asn Lys Thr Val Lys Gln Ile Met Leu Met Ser
305                 310                 315                 320
Gly His Val Phe His Ser His Tyr Gln Pro Ile Asn Lys Arg Pro Arg
                325                 330                 335
Gln Ala Trp Cys Trp Phe Lys Gly Lys Trp Lys Asp Ala Met Gln Glu
            340                 345                 350
Val Lys Glu Thr Leu Ala Lys His Pro Arg Tyr Arg Gly Thr Asn Asp
        355                 360                 365
Thr Arg Asn Ile Ser Phe Ala Ala Pro Gly Lys Gly Ser Asp Pro Glu
370                 375                 380
Val Ala Tyr Met Trp Thr Asn Cys Arg Gly Glu Phe Leu Tyr Cys Asn
385                 390                 395                 400
Met Thr Trp Phe Leu Asn Trp Ile Glu Asn Lys Thr His Arg Asn Tyr
                405                 410                 415
Ala Pro Cys His Ile Lys Gln Ile Ile Asn Thr Trp His Lys Val Gly
            420                 425                 430
Arg Asn Val Tyr Leu Pro Pro Arg Glu Gly Glu Leu Ser Cys Asn Ser
        435                 440                 445
Thr Val Thr Ser Ile Ile Ala Asn Met Asp Trp Gln Asn Asn Asn Gln
    450                 455                 460
Thr Asn Ile Thr Phe Ser Ala Glu Val Ala Glu Leu Tyr Arg Leu Glu
465                 470                 475                 480
Leu Gly Asp Tyr Lys Leu Val Glu Ile Thr Pro Ile Gly Phe Ala Pro
                485                 490                 495
Thr Lys Glu Lys Arg Tyr Ser Ser Ala His Gly Arg His Thr Arg Gly
            500                 505                 510
Val Phe Val Leu Gly Phe Leu Gly Phe Leu Ala Thr Ala Gly Ser Ala
        515                 520                 525
```

```
Met Gly Ala Ala Ser Leu Thr Val Ser Ala Gln Ser Arg Thr Leu Leu
            530                 535                 540

Ala Gly Ile Val Gln Gln Gln Gln Leu Leu Asp Val Val Lys Arg
545                 550                 555                 560

Gln Gln Glu Leu Leu Arg Leu Thr Val Trp Gly Thr Lys Asn Leu Gln
                565                 570                 575

Ala Arg Val Thr Ala Ile Glu Lys Tyr Leu Gln Asp Gln Ala Arg Leu
            580                 585                 590

Asn Ser Trp Gly Cys Ala Phe Arg Gln Val Cys His Thr Thr Val Pro
            595                 600                 605

Trp Val Asn Asp Ser Leu Ala Pro Asp Trp Asp Asn Met Thr Trp Gln
            610                 615                 620

Glu Trp Glu Lys Gln Val Arg Tyr Leu Glu Ala Asn Ile Ser Lys Ser
625                 630                 635                 640

Leu Glu Gln Ala Gln Ile Gln Gln Glu Lys Asn Met Tyr Glu Leu Gln
                645                 650                 655

Lys Leu Asn Ser Trp Asp Ile Phe Gly Asn Trp Phe Asp Leu Thr Ser
            660                 665                 670

Trp Val Lys Tyr Ile Gln Tyr Gly Val Leu Ile Ile Val Ala Val Ile
            675                 680                 685

Ala Leu Arg Ile Val Ile Tyr Val Val Gln Met Leu Ser Arg Leu Arg
690                 695                 700

Lys Gly Tyr Arg Pro Val Phe Ser Ser Pro Gly Tyr Ile Gln Gln
705                 710                 715                 720

Ile His Ile His Lys Asp Arg Gly Gln Pro Ala Asn Glu Glu Thr Glu
                725                 730                 735

Glu Asp Gly Gly Ser Asn Gly Gly Asp Arg Tyr Trp Pro Trp Pro Ile
            740                 745                 750

Ala Tyr Ile His Phe Leu Ile Arg Gln Leu Ile Arg Leu Leu Thr Arg
            755                 760                 765

Leu Tyr Ser Ile Cys Arg Asp Leu Leu Ser Arg Ser Phe Leu Thr Leu
            770                 775                 780

Gln Leu Ile Tyr Gln Asn Leu Arg Asp Trp Leu Arg Leu Arg Thr Ala
785                 790                 795                 800

Phe Leu Gln Tyr Gly Cys Glu Trp Ile Gln Glu Ala Phe Gln Ala Ala
                805                 810                 815

Ala Arg Ala Thr Arg Glu Thr Leu Ala Gly Ala Cys Arg Gly Leu Trp
            820                 825                 830

Arg Val Leu Glu Arg Ile Gly Arg Gly Ile Leu Ala Val Pro Arg Arg
            835                 840                 845

Ile Arg Gln Gly Ala Glu Ile Ala Leu Leu
850                 855
```

(2) INFORMATION FOR SEQ ID NO:18:

(i) SEQUENCE CHARACTERISTICS:
        (A) LENGTH: 2531 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 12..2531

(xi) SEQUENCE DESCRIPTION: SEQ ID NO:18:

```
CTGCAGTGAC A ATG AGA GTG AAG GAG AAA TAT CAG CAC TTG TGG AGA TGG      50
             Met Arg Val Lys Glu Lys Tyr Gln His Leu Trp Arg Trp
              1               5                  10

GGG TGG AAA TGG GGC ACC ATG CTC CTT GGG ATA TTG ATG ATC TGT AGT        98
Gly Trp Lys Trp Gly Thr Met Leu Leu Gly Ile Leu Met Ile Cys Ser
     15              20                  25

GCT ACA GAA AAA TTG TGG GTC ACA GTC TAT TAT GGG GTA CCT GTG TGG       146
Ala Thr Glu Lys Leu Trp Val Thr Val Tyr Tyr Gly Val Pro Val Trp
 30              35                  40                  45

AAG GAA GCA ACC ACC ACT CTA TTT TGT GCA TCA GAT GCT AAA CCA TAT       194
Lys Glu Ala Thr Thr Thr Leu Phe Cys Ala Ser Asp Ala Lys Pro Tyr
                 50                  55                  60

GAT ACA GAG GTA CAT AAT GTT TGG GCC ACA CAT GCC TGT GTA CCC ACA       242
Asp Thr Glu Val His Asn Val Trp Ala Thr His Ala Cys Val Pro Thr
                     65                  70                  75

GAC CCC AAC CCA CAA GAA GTA GTA TTG GTA AAT GTG ACA GAA AAT TTT       290
Asp Pro Asn Pro Gln Glu Val Val Leu Val Asn Val Thr Glu Asn Phe
                 80                  85                  90

AAC ATG TGG AAA AAT GAC ATG GTA GAA CAG ATG CAT GAG GAT ATA ATC       338
Asn Met Trp Lys Asn Asp Met Val Glu Gln Met His Glu Asp Ile Ile
         95                 100                 105

AGT TTA TGG GAT CAA AGC CTA AAG CCA TGT GTA AAA TTA ACC CCA CTC       386
Ser Leu Trp Asp Gln Ser Leu Lys Pro Cys Val Lys Leu Thr Pro Leu
110             115                 120                 125

TGT GTT AGT TTA AAG TGC ACT GAT TTG GGG AAT GCT ACT AAT ACC AAT       434
Cys Val Ser Leu Lys Cys Thr Asp Leu Gly Asn Ala Thr Asn Thr Asn
                130                 135                 140

AGT AGT AAT ACC AAT AGT AGT AGC GGG GAA ATG ATG ATG GAG AAA GGA       482
Ser Ser Asn Thr Asn Ser Ser Ser Gly Glu Met Met Met Glu Lys Gly
                145                 150                 155

GAG ATA AAA AAC TGC TCT TTC AAT ATC AGC ACA AGC ATA AGA GGT AAG       530
Glu Ile Lys Asn Cys Ser Phe Asn Ile Ser Thr Ser Ile Arg Gly Lys
            160                 165                 170

GTG CAG AAA GAA TAT GCA TTT TTT TAT AAA CTT GAT ATA ATA CCA ATA       578
Val Gln Lys Glu Tyr Ala Phe Phe Tyr Lys Leu Asp Ile Ile Pro Ile
        175                 180                 185

GAT AAT GAT ACT ACC AGC TAT ACG TTG ACA AGT TGT AAC ACC TCA GTC       626
Asp Asn Asp Thr Thr Ser Tyr Thr Leu Thr Ser Cys Asn Thr Ser Val
190                 195                 200                 205

ATT ACA CAG GCC TGT CCA AAG GTA TCC TTT GAG CCA ATT CCC ATA CAT       674
Ile Thr Gln Ala Cys Pro Lys Val Ser Phe Glu Pro Ile Pro Ile His
                210                 215                 220

TAT TGT GCC CCG GCT GGT TTT GCG ATT CTA AAA TGT AAT AAT AAG ACG       722
Tyr Cys Ala Pro Ala Gly Phe Ala Ile Leu Lys Cys Asn Asn Lys Thr
                225                 230                 235

TTC AAT GGA ACA GGA CCA TGT ACA AAT GTC AGC ACA GTA CAA TGT ACA       770
Phe Asn Gly Thr Gly Pro Cys Thr Asn Val Ser Thr Val Gln Cys Thr
                240                 245                 250

CAT GGA ATT AGG CCA GTA GTA TCA ACT CAA CTG CTG TTG AAT GGC AGT       818
His Gly Ile Arg Pro Val Val Ser Thr Gln Leu Leu Leu Asn Gly Ser
        255                 260                 265

CTA GCA GAA GAA GAG GTA GTA ATT AGA TCT GCC AAT TTC ACA GAC AAT       866
Leu Ala Glu Glu Glu Val Val Ile Arg Ser Ala Asn Phe Thr Asp Asn
270                 275                 280                 285

GCT AAA ACC ATA ATA GTA CAG CTG AAC CAA TCT GTA GAA ATT AAT TGT       914
Ala Lys Thr Ile Ile Val Gln Leu Asn Gln Ser Val Glu Ile Asn Cys
                290                 295                 300

ACA AGA CCC AAC AAC AAT ACA AGA AAA AGT ATC CGT ATC CAG AGG GGA       962
Thr Arg Pro Asn Asn Asn Thr Arg Lys Ser Ile Arg Ile Gln Arg Gly
```

```
                      305                 310                 315
CCA GGG AGA GCA TTT GTT ACA ATA GGA AAA ATA GGA AAT ATG AGA CAA    1010
Pro Gly Arg Ala Phe Val Thr Ile Gly Lys Ile Gly Asn Met Arg Gln
        320                 325                 330

GCA CAT TGT AAC ATT AGT AGA CCA AAA TGG AAT GCC ACT TTA AAA CAG    1058
Ala His Cys Asn Ile Ser Arg Pro Lys Trp Asn Ala Thr Leu Lys Gln
        335                 340                 345

ATA GCT AGC AAA TTA AGA GAA CAA TTT GGA AAT AAT AAA ACA ATA ATC    1106
Ile Ala Ser Lys Leu Arg Glu Gln Phe Gly Asn Asn Lys Thr Ile Ile
350                 355                 360                 365

TTT AAG CAA TCC TCA GGA GGG GAC CCA GAA ATT GTA ACG CAC AGT TTT    1154
Phe Lys Gln Ser Ser Gly Gly Asp Pro Glu Ile Val Thr His Ser Phe
                370                 375                 380

AAT TGT GGA GGG GAA TTT TTC TAC TGT AAT TCA ACA CAA CTG TTT AAT    1202
Asn Cys Gly Gly Glu Phe Phe Tyr Cys Asn Ser Thr Gln Leu Phe Asn
                385                 390                 395

AGT ACT TGG TTT AAT AGT ACT TGG AGT ACT GAA GGG TCA AAT AAC ACT    1250
Ser Thr Trp Phe Asn Ser Thr Trp Ser Thr Glu Gly Ser Asn Asn Thr
            400                 405                 410

GAA GGA AGT GAC ACA ATC ACA CTC CCA TGC AGA ATA AAA CAA TTT ATA    1298
Glu Gly Ser Asp Thr Ile Thr Leu Pro Cys Arg Ile Lys Gln Phe Ile
        415                 420                 425

AAC ATG TGG CAG GAA GTA GGA AAA GCA ATC TAT GCC CCT CCC ATC AGC    1346
Asn Met Trp Gln Glu Val Gly Lys Ala Ile Tyr Ala Pro Pro Ile Ser
430                 435                 440                 445

GGA CAA ATT AGA TGT TCA TCA AAT ATT ACA GGG CTG CTA TTA ACA AGA    1394
Gly Gln Ile Arg Cys Ser Ser Asn Ile Thr Gly Leu Leu Leu Thr Arg
                450                 455                 460

GAT GGT GGT AAT AAC AAC AAT GGG TCC GAG ATC TTC AGA CCT GGA GGA    1442
Asp Gly Gly Asn Asn Asn Asn Gly Ser Glu Ile Phe Arg Pro Gly Gly
                465                 470                 475

GGA GAT ATG AGG GAC AAT TGG AGA AGT GAA TTA TAT AAA TAT AAA GTA    1490
Gly Asp Met Arg Asp Asn Trp Arg Ser Glu Leu Tyr Lys Tyr Lys Val
            480                 485                 490

GTA AAA ATT GAA CCA TTA GGA GTA GCA CCC ACC AAG GCA CAG AAT CAC    1538
Val Lys Ile Glu Pro Leu Gly Val Ala Pro Thr Lys Ala Gln Asn His
        495                 500                 505

GTG GTG CAG AAT GAA CAC CAA GCA GTG GGA ATA GGA GCT TTG TTC CTT    1586
Val Val Gln Asn Glu His Gln Ala Val Gly Ile Gly Ala Leu Phe Leu
510                 515                 520                 525

GGG TTC TTG GGA GCA GCA GGA AGC ACT ATG GGC GCA CGG TCA ATG ACG    1634
Gly Phe Leu Gly Ala Ala Gly Ser Thr Met Gly Ala Arg Ser Met Thr
                530                 535                 540

CTG ACG GTA CAG GCC AGA CAA TTA TTG TCT GGT ATA GTG CAG CAG CAG    1682
Leu Thr Val Gln Ala Arg Gln Leu Leu Ser Gly Ile Val Gln Gln Gln
                545                 550                 555

AAC AAT TTG CTG AGG GCT ATT GAG GCG CAA CAG CAT CTG TTG CAA CTC    1730
Asn Asn Leu Leu Arg Ala Ile Glu Ala Gln Gln His Leu Leu Gln Leu
            560                 565                 570

ACA GTC TGG GGC ATC AAG CAG CTC CAG GCA AGA ATC CTG GCT GTG GAA    1778
Thr Val Trp Gly Ile Lys Gln Leu Gln Ala Arg Ile Leu Ala Val Glu
        575                 580                 585

AGA TAC CTA AAG GAT CAA CAG CTC CTG GGG ATT TGG GGT TGC TCT GGA    1826
Arg Tyr Leu Lys Asp Gln Gln Leu Leu Gly Ile Trp Gly Cys Ser Gly
590                 595                 600                 605

AAA CTC ATT TGC ACC ACT GCT GTG CCT TGG AAT GCT AGT TGG AGT AAT    1874
Lys Leu Ile Cys Thr Thr Ala Val Pro Trp Asn Ala Ser Trp Ser Asn
                610                 615                 620

AAA TCT CTG GAA CAG ATT TGG AAT AAC ATG ACC TGG ATG GAG TGG GAC    1922
```

-continued

```
Lys Ser Leu Glu Gln Ile Trp Asn Asn Met Thr Trp Met Glu Trp Asp
            625                 630                 635

AGA GAA ATT AAC AAT TAC ACA AGC TTA ATA CAT TCC TTA ATT GAA GAA    1970
Arg Glu Ile Asn Asn Tyr Thr Ser Leu Ile His Ser Leu Ile Glu Glu
            640                 645                 650

TCG CAA AAC CAG CAA GAA AAG AAT CAA CAA GAA TTA TTG GAA TTA GAT    2018
Ser Gln Asn Gln Gln Glu Lys Asn Gln Gln Glu Leu Leu Glu Leu Asp
655                 660                 665

AAA TGG GCA AGT TTG TGG AAT TGG TTT AAC ATA ACA AAT TGG CTG TGG    2066
Lys Trp Ala Ser Leu Trp Asn Trp Phe Asn Ile Thr Asn Trp Leu Trp
670                 675                 680                 685

TAT ATA AAA AAT AGA GTT AGG CAG GGA TAT TCA CCA TTA TCG TTT CAG    2114
Tyr Ile Lys Asn Arg Val Arg Gln Gly Tyr Ser Pro Leu Ser Phe Gln
                690                 695                 700

ACC CAC CTC CCA ACC CCG AGG GGA CCC GAC AGG CCC GAA GGA ATA GAA    2162
Thr His Leu Pro Thr Pro Arg Gly Pro Asp Arg Pro Glu Gly Ile Glu
                705                 710                 715

GAA GAA GGT GGA GAG AGA GAC AGA GAC AGA TCC ATT CGA TTA GTG AAC    2210
Glu Glu Gly Gly Glu Arg Asp Arg Asp Arg Ser Ile Arg Leu Val Asn
                720                 725                 730

GGA TCC TTA GCA CTT ATC TGG GAC GAT CTG CGG AGC CTG TGC CTC TTC    2258
Gly Ser Leu Ala Leu Ile Trp Asp Asp Leu Arg Ser Leu Cys Leu Phe
735                 740                 745

AGC TAC CAC CGC TTG AGA GAC TTA CTC TTG ATT GTA ACG AGG ATT GTG    2306
Ser Tyr His Arg Leu Arg Asp Leu Leu Leu Ile Val Thr Arg Ile Val
750                 755                 760                 765

GAA CTT CTG GGA CGC AGG GGG TGG GAA GCC CTC AAA TAT TGG TGG AAT    2354
Glu Leu Leu Gly Arg Arg Gly Trp Glu Ala Leu Lys Tyr Trp Trp Asn
                770                 775                 780

CTC CTA CAG TAT TGG AGT CAG GAA CTA AAG AAT AGT GCT GTT AGC TTG    2402
Leu Leu Gln Tyr Trp Ser Gln Glu Leu Lys Asn Ser Ala Val Ser Leu
                785                 790                 795

CTC AAT GCC ACA GCC ATA GCA GTA GCT GAG GGG ACA GAT AGG GTT ATA    2450
Leu Asn Ala Thr Ala Ile Ala Val Ala Glu Gly Thr Asp Arg Val Ile
                800                 805                 810

GAA GTA GTA CAA GGA GCT TGT AGA GCT ATT CGC CAC ATA CCT AGA AGA    2498
Glu Val Val Gln Gly Ala Cys Arg Ala Ile Arg His Ile Pro Arg Arg
815                 820                 825

ATA AGA CAG GGC TTG GAA AGG ATT TTG CTA TAA                         2531
Ile Arg Gln Gly Leu Glu Arg Ile Leu Leu
830                 835                 840
```

(2) INFORMATION FOR SEQ ID NO:19:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..27

(xi) SEQUENCE DESCRIPTION: SEQ ID NO:19:

```
GAT GGG TGG CAA GTG GTC AAA AAG TAG                                 27
Asp Gly Trp Gln Val Val Lys Lys
1                   5
```

(2) INFORMATION FOR SEQ ID NO:20:

(i) SEQUENCE CHARACTERISTICS:
    (A) LENGTH: 86 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: CDS
    (B) LOCATION: 1..42

(xi) SEQUENCE DESCRIPTION: SEQ ID NO:20:

```
TGT GGT TGG ATG GCC TAC TGT AAG GGA AAG AAT GAG ACG AGC          42
Cys Gly Trp Met Ala Tyr Cys Lys Gly Lys Asn Glu Thr Ser
 1               5                  10

TGAGCCAGCA GCAGATGGGG TGGGAGCAGC ATCTCGACCT GCAG                 86
```

(2) INFORMATION FOR SEQ ID NO:21:

(i) SEQUENCE CHARACTERISTICS:
    (A) LENGTH: 1539 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: CDS
    (B) LOCATION: 1..1539

(xi) SEQUENCE DESCRIPTION: SEQ ID NO:21:

```
ATG AGA GTG AAG GGG ATC AGG AGG AAT TAT CAG CAC TGG TGG GGA TCG          48
Met Arg Val Lys Gly Ile Arg Arg Asn Tyr Gln His Trp Trp Gly Ser
 1               5                  10                  15

GGC ACG ATG CTC CTT GGG TTA TTA ATG ATC TGT AGT GCT ACA GAA AAA          96
Gly Thr Met Leu Leu Gly Leu Leu Met Ile Cys Ser Ala Thr Glu Lys
                20                  25                  30

TTG TGG GTC ACA GTC TAT TAT GGG GTA CCT GTG TGG AAA GAA GCA ACC         144
Leu Trp Val Thr Val Tyr Tyr Gly Val Pro Val Trp Lys Glu Ala Thr
                35                  40                  45

ACC ACT CTA TTT TGT GCA TCA GAT GCT AAA GCA TAT GAT ACA GAG GTA         192
Thr Thr Leu Phe Cys Ala Ser Asp Ala Lys Ala Tyr Asp Thr Glu Val
     50                  55                  60

CAT AAT GTT TGG GCC ACA CAA GCC TGT GTA CCC ACA GAC CCC AAC CCA         240
His Asn Val Trp Ala Thr Gln Ala Cys Val Pro Thr Asp Pro Asn Pro
 65                  70                  75                  80

CAA GAA GTA GAA TTG GTA AAT GTG ACA GAA AAT TTT AAC ATG TGG AAA         288
Gln Glu Val Glu Leu Val Asn Val Thr Glu Asn Phe Asn Met Trp Lys
                 85                  90                  95

AAT AAC ATG GTA GAA CAG ATG CAT GAG GAT ATA ATC AGT TTA TGG GAT         336
Asn Asn Met Val Glu Gln Met His Glu Asp Ile Ile Ser Leu Trp Asp
                100                 105                 110

CAA AGC CTA AAG CCA TGT GTA AAA TTA ACC CCA CTC TGT GTT ACT TTA         384
Gln Ser Leu Lys Pro Cys Val Lys Leu Thr Pro Leu Cys Val Thr Leu
            115                 120                 125

AAT TGC ACT GAT TTG AGG AAT ACT ACT AAT ACC AAT AAT AGT ACT GCT         432
Asn Cys Thr Asp Leu Arg Asn Thr Thr Asn Thr Asn Asn Ser Thr Ala
        130                 135                 140

AAT AAC AAT AGT AAT AGC GAG GGA ACA ATA AAG GGA GGA GAA ATG AAA         480
Asn Asn Asn Ser Asn Ser Glu Gly Thr Ile Lys Gly Gly Glu Met Lys
145                 150                 155                 160

AAC TGC TCT TTC AAT ATC ACC ACA AGC ATA AGA GAT AAG ATG CAG AAA         528
Asn Cys Ser Phe Asn Ile Thr Thr Ser Ile Arg Asp Lys Met Gln Lys
```

```
                    165              170              175
GAA TAT GCA CTT CTT TAT AAA CTT GAT ATA GTA TCA ATA GAT AAT GAT       576
Glu Tyr Ala Leu Leu Tyr Lys Leu Asp Ile Val Ser Ile Asp Asn Asp
            180              185              190

AGT ACC AGC TAT AGG TTG ATA AGT TGT AAT ACC TCA GTC ATT ACA CAA       624
Ser Thr Ser Tyr Arg Leu Ile Ser Cys Asn Thr Ser Val Ile Thr Gln
        195              200              205

GCT TGT CCA AAG ATA TCC TTT GAG CCA ATT CCC ATA CAC TAT TGT GCC       672
Ala Cys Pro Lys Ile Ser Phe Glu Pro Ile Pro Ile His Tyr Cys Ala
        210              215              220

CCG GCT GGT TTT GCG ATT CTA AAA TGT AAC GAT AAA AAG TTC AGT GGA       720
Pro Ala Gly Phe Ala Ile Leu Lys Cys Asn Asp Lys Lys Phe Ser Gly
225              230              235              240

AAA GGA TCA TGT AAA AAT GTC AGC ACA GTA CAA TGT ACA CAT GGA ATT       768
Lys Gly Ser Cys Lys Asn Val Ser Thr Val Gln Cys Thr His Gly Ile
            245              250              255

AGG CCA GTA GTA TCA ACT CAA CTG CTG TTA AAT GGC AGT CTA GCA GAA       816
Arg Pro Val Val Ser Thr Gln Leu Leu Leu Asn Gly Ser Leu Ala Glu
        260              265              270

GAA GAG GTA GTA ATT AGA TCT GAG AAT TTC ACT GAT AAT GCT AAA ACC       864
Glu Glu Val Val Ile Arg Ser Glu Asn Phe Thr Asp Asn Ala Lys Thr
        275              280              285

ATC ATA GTA CAT CTG AAT GAA TCG GTA CAA ATT AAT TGT ACA AGA CCC       912
Ile Ile Val His Leu Asn Glu Ser Val Gln Ile Asn Cys Thr Arg Pro
290              295              300

AAC TAC AAT AAA AGA AAA AGG ATA CAT ATA GGA CCA GGG AGA GCA TTT       960
Asn Tyr Asn Lys Arg Lys Arg Ile His Ile Gly Pro Gly Arg Ala Phe
305              310              315              320

TAT ACA ACA AAA AAT ATA ATA GGA ACT ATA AGA CAA GCA CAT TGT AAC      1008
Tyr Thr Thr Lys Asn Ile Ile Gly Thr Ile Arg Gln Ala His Cys Asn
            325              330              335

ATT AGT AGA GCA AAA TGG AAT GAC ACT TTA AGA CAG ATA GTT AGC AAA      1056
Ile Ser Arg Ala Lys Trp Asn Asp Thr Leu Arg Gln Ile Val Ser Lys
            340              345              350

TTA AAA GAA CAA TTT AAG AAT AAA ACA ATA GTC TTT AAT CAA TCC TCA      1104
Leu Lys Glu Gln Phe Lys Asn Lys Thr Ile Val Phe Asn Gln Ser Ser
        355              360              365

GGA GGG GAC CCA GAA ATT GTA ATG CAC AGT TTT AAT TGT GGA GGG GAA      1152
Gly Gly Asp Pro Glu Ile Val Met His Ser Phe Asn Cys Gly Gly Glu
        370              375              380

TTT TTC TAC TGT AAT ACA TCA CCA CTG TTT AAT AGT ACT TGG AAT GGT      1200
Phe Phe Tyr Cys Asn Thr Ser Pro Leu Phe Asn Ser Thr Trp Asn Gly
385              390              395              400

AAT AAT ACT TGG AAT AAT ACT ACA GGG TCA AAT AAC AAT ATC ACA CTT      1248
Asn Asn Thr Trp Asn Asn Thr Thr Gly Ser Asn Asn Asn Ile Thr Leu
            405              410              415

CAA TGC AAA ATA AAA CAA ATT ATA AAC ATG TGG CAG GAA GTA GGA AAA      1296
Gln Cys Lys Ile Lys Gln Ile Ile Asn Met Trp Gln Glu Val Gly Lys
            420              425              430

GCA ATG TAT GCC CCT CCC ATT GAA GGA CAA ATT AGA TGT TCA TCA AAT      1344
Ala Met Tyr Ala Pro Pro Ile Glu Gly Gln Ile Arg Cys Ser Ser Asn
            435              440              445

ATT ACA GGG CTA CTA TTA ACA AGA GAT GGT GGT AAG GAC ACG GAC ACG      1392
Ile Thr Gly Leu Leu Leu Thr Arg Asp Gly Gly Lys Asp Thr Asp Thr
        450              455              460

AAC GAC ACC GAG ATC TTC AGA CCT GGA GGA GGA GAT ATG AGG GAC AAT      1440
Asn Asp Thr Glu Ile Phe Arg Pro Gly Gly Gly Asp Met Arg Asp Asn
465              470              475              480

TGG AGA AGT GAA TTA TAT AAA TAT AAA GTA GTA ACA ATT GAA CCA TTA      1488
```

```
Trp Arg Ser Glu Leu Tyr Lys Tyr Lys Val Val Thr Ile Glu Pro Leu
            485                 490                 495

GGA GTA GCA CCC ACC AAG GCA AAG AGA AGA GTG GTG CAG AGA GAA AAA        1536
Gly Val Ala Pro Thr Lys Ala Lys Arg Arg Val Val Gln Arg Glu Lys
            500                 505                 510

AGA                                                                    1539
Arg (2) INFORMATION FOR SEQ ID NO:22:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

GGCAGCATGC TCCTTGGGAT ATTGATGATC TG                                     32

(2) INFORMATION FOR SEQ ID NO:23:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

CTTGGTAATC TCATCGTGG GTGGGCCCGT TTC                                     33

(2) INFORMATION FOR SEQ ID NO:24:

(i) SEQUENCE CHARACTERISTICS:
        (A) LENGTH: 1524 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1524

(xi) SEQUENCE DESCRIPTION: SEQ ID NO:24:

ATG AGA GCG AGG GGG ATA GAG AGA AAT TGT CAA AAC TGG TGG AAA TGG         48
Met Arg Ala Arg Gly Ile Glu Arg Asn Cys Gln Asn Trp Trp Lys Trp
 1               5                  10                  15

GGC ATC ATG CTC CTT GGG ATA TTG ATG ACC TGT AGT GCT GCA GAC AAT         96
Gly Ile Met Leu Leu Gly Ile Leu Met Thr Cys Ser Ala Ala Asp Asn
                20                  25                  30

CTG TGG GTC ACA GTT TAT TAT GGG GTG CCT GTA TGG AAG GAA GCA ACC        144
Leu Trp Val Thr Val Tyr Tyr Gly Val Pro Val Trp Lys Glu Ala Thr
            35                  40                  45

ACC ACT CTA TTT TGT GCA TCA GAT GCT AAA TCA TAT GAA ACA GAG GCA        192
Thr Thr Leu Phe Cys Ala Ser Asp Ala Lys Ser Tyr Glu Thr Glu Ala
    50                  55                  60

CAT AAT ATC TGG GCC ACA CAT GCC TGT GTA CCC ACG GAC CCC AAC CCA        240
His Asn Ile Trp Ala Thr His Ala Cys Val Pro Thr Asp Pro Asn Pro
65                  70                  75                  80

CAA GAA ATA GCA CTG GAA AAT GTG ACA GAA AAC TTT AAC ATG TGG AAA        288
Gln Glu Ile Ala Leu Glu Asn Val Thr Glu Asn Phe Asn Met Trp Lys
```

```
                     85                    90                        95
AAT AAC ATG GTG GAA CAG ATG CAT GAG GAT ATA ATC AGT TTA TGG GAT       336
Asn Asn Met Val Glu Gln Met His Glu Asp Ile Ile Ser Leu Trp Asp
            100                 105                 110

CAA AGC CTA AAA CCA TGT GTA AAA TTA ACC CCA CTC TGT GTC ACT TTA       384
Gln Ser Leu Lys Pro Cys Val Lys Leu Thr Pro Leu Cys Val Thr Leu
        115                 120                 125

AAC TGT AGT GAT GAA TTG AGG AAC AAT GGC ACT ATG GGG AAC AAT GTC       432
Asn Cys Ser Asp Glu Leu Arg Asn Asn Gly Thr Met Gly Asn Asn Val
    130                 135                 140

ACT ACA GAG GAG AAA GGA ATG AAA AAC TGC TCT TTC AAT GTA ACC ACA       480
Thr Thr Glu Glu Lys Gly Met Lys Asn Cys Ser Phe Asn Val Thr Thr
145                 150                 155                 160

GTA CTA AAA GAT AAG AAG CAG CAA GTA TAT GCA CTT TTT TAT AGA CTT       528
Val Leu Lys Asp Lys Lys Gln Gln Val Tyr Ala Leu Phe Tyr Arg Leu
            165                 170                 175

GAT ATA GTA CCA ATA GAC AAT GAT AGT AGT ACC AAT AGT ACC AAT TAT       576
Asp Ile Val Pro Ile Asp Asn Asp Ser Ser Thr Asn Ser Thr Asn Tyr
        180                 185                 190

AGG TTA ATA AAT TGT AAT ACC TCA GCC ATT ACA CAG GCT TGT CCA AAG       624
Arg Leu Ile Asn Cys Asn Thr Ser Ala Ile Thr Gln Ala Cys Pro Lys
    195                 200                 205

GTA TCC TTT GAG CCA ATT CCC ATA CAT TAT TGT GCC CCA GCT GGT TTT       672
Val Ser Phe Glu Pro Ile Pro Ile His Tyr Cys Ala Pro Ala Gly Phe
210                 215                 220

GCG ATT CTA AAG TGT AGA GAT AAG AAG TTC AAT GGA ACA GGC CCA TGC       720
Ala Ile Leu Lys Cys Arg Asp Lys Lys Phe Asn Gly Thr Gly Pro Cys
225                 230                 235                 240

ACA AAT GTC AGC ACA GTA CAA TGT ACA CAT GGA ATT AGG CCA GTG GTG       768
Thr Asn Val Ser Thr Val Gln Cys Thr His Gly Ile Arg Pro Val Val
            245                 250                 255

TCA ACT CAA CTG CTG TTG AAT GGC AGT CTA GCA GAA GAA GAG GTC ATA       816
Ser Thr Gln Leu Leu Leu Asn Gly Ser Leu Ala Glu Glu Glu Val Ile
        260                 265                 270

ATT AGA TCC GAA AAT CTC ACA AAC AAT GCT AAA AAC ATA ATA GCA CAT       864
Ile Arg Ser Glu Asn Leu Thr Asn Asn Ala Lys Asn Ile Ile Ala His
    275                 280                 285

CTT AAT GAA TCT GTA AAA ATT ACC TGT GCA AGG CCC TAT CAA AAT ACA       912
Leu Asn Glu Ser Val Lys Ile Thr Cys Ala Arg Pro Tyr Gln Asn Thr
290                 295                 300

AGA CAA AGA ACA CCT ATA GGA CTA GGG CAA TCA CTC TAT ACT ACA AGA       960
Arg Gln Arg Thr Pro Ile Gly Leu Gly Gln Ser Leu Tyr Thr Thr Arg
305                 310                 315                 320

TCA AGA TCA ATA ATA GGA CAA GCA CAT TGT AAT ATT AGT AGA GCA CAA       1008
Ser Arg Ser Ile Ile Gly Gln Ala His Cys Asn Ile Ser Arg Ala Gln
            325                 330                 335

TGG AGT AAA ACT TTA CAA CAA GTA GCT AGA AAA TTA GGA ACC CTT CTT       1056
Trp Ser Lys Thr Leu Gln Gln Val Ala Arg Lys Leu Gly Thr Leu Leu
        340                 345                 350

AAC AAA ACA ATA ATA AAG TTT AAA CCA TCC TCA GGA GGG GAC CCA GAA       1104
Asn Lys Thr Ile Ile Lys Phe Lys Pro Ser Ser Gly Gly Asp Pro Glu
    355                 360                 365

ATT ACA ACA CAC AGT TTT AAT TGT GGA GGG GAA TTC TTC TAC TGT AAT       1152
Ile Thr Thr His Ser Phe Asn Cys Gly Gly Glu Phe Phe Tyr Cys Asn
370                 375                 380

ACA TCA GGA CTG TTT AAT AGT ACA TGG AAT ATT AGT GCA TGG AAT AAT       1200
Thr Ser Gly Leu Phe Asn Ser Thr Trp Asn Ile Ser Ala Trp Asn Asn
385                 390                 395                 400

ATT ACA GAG TCA AAT AAT AGC ACA AAC ACA AAC ATC ACA CTC CAA TGC       1248
```

```
Ile Thr Glu Ser Asn Asn Ser Thr Asn Thr Asn Ile Thr Leu Gln Cys
            405                 410                 415

AGA ATA AAA CAA ATT ATA AAG ATG GTG GCA GGC AGG AAA GCA ATA TAT        1296
Arg Ile Lys Gln Ile Ile Lys Met Val Ala Gly Arg Lys Ala Ile Tyr
            420                 425                 430

GCC CCT CCT ATC GAA AGA AAC ATT CTA TGT TCA TCA AAT ATT ACA GGG        1344
Ala Pro Pro Ile Glu Arg Asn Ile Leu Cys Ser Ser Asn Ile Thr Gly
            435                 440                 445

CTA CTA TTG ACA AGA GAT GGT GGT ATA AAT AAT AGT ACT AAC GAG ACC        1392
Leu Leu Leu Thr Arg Asp Gly Gly Ile Asn Asn Ser Thr Asn Glu Thr
        450                 455                 460

TTT AGA CCT GGA GGA GGA GAT ATG AGG GAC AAT TGG AGA AGT GAA TTA        1440
Phe Arg Pro Gly Gly Gly Asp Met Arg Asp Asn Trp Arg Ser Glu Leu
465                 470                 475                 480

TAT AAA TAT AAG GTA GTA CAA ATT GAA CCA CTA GGA GTA GCA CCC ACC        1488
Tyr Lys Tyr Lys Val Val Gln Ile Glu Pro Leu Gly Val Ala Pro Thr
                485                 490                 495

AGG GCA AAG AGA AGA GTG GTG GAA AGA GAA AAA AGA                        1524
Arg Ala Lys Arg Arg Val Val Glu Arg Glu Lys Arg
                500                 505

(2) INFORMATION FOR SEQ ID NO:25:

(i) SEQUENCE CHARACTERISTICS:
        (A) LENGTH: 1557 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1557

(xi) SEQUENCE DESCRIPTION: SEQ ID NO:25:

ATG AGA GTG ATG GAG ATG AGG AAG AAT TGT CAG CAC TTG TGG AAA TGG          48
Met Arg Val Met Glu Met Arg Lys Asn Cys Gln His Leu Trp Lys Trp
1               5                   10                  15

GGC ACC ATG CTC CTT GGG ATG TTG ATG ATC TGT AGT GCT GCA GAG GAC         96
Gly Thr Met Leu Leu Gly Met Leu Met Ile Cys Ser Ala Ala Glu Asp
                20                  25                  30

TTG TGG GTC ACA GTC TAT TAT GGG GTA CCT GTG TGG AAA GAA GCA ACC        144
Leu Trp Val Thr Val Tyr Tyr Gly Val Pro Val Trp Lys Glu Ala Thr
            35                  40                  45

ACC ACT CTA TTT TGT GCA TCA GAA GCT AAA GCA TAT AAA ACA GAG GTA        192
Thr Thr Leu Phe Cys Ala Ser Glu Ala Lys Ala Tyr Lys Thr Glu Val
        50                  55                  60

CAT AAT GTC TGG GCC AAA CAT GCT TGT GTA CCT ACA GAC CCC AAC CCA        240
His Asn Val Trp Ala Lys His Ala Cys Val Pro Thr Asp Pro Asn Pro
65                  70                  75                  80

CAA GAA GTA CTA TTG GAA AAT GTG ACA GAA AAT TTT AAC ATG TGG AAA        288
Gln Glu Val Leu Leu Glu Asn Val Thr Glu Asn Phe Asn Met Trp Lys
                85                  90                  95

AAT AAC ATG GTA GAA CAG ATG CAT GAG GAT ATA ATC AGT TTA TGG GAT        336
Asn Asn Met Val Glu Gln Met His Glu Asp Ile Ile Ser Leu Trp Asp
                100                 105                 110

CAA AGC CTA AAG CCA TGT GTA AAA TTA ACC CCA CTC TGT GTT ACT TTA        384
Gln Ser Leu Lys Pro Cys Val Lys Leu Thr Pro Leu Cys Val Thr Leu
            115                 120                 125

AAT TGC ACT GAT GCT AAC TTG AAT GGT ACT AAT GTC ACT AGT AGT AGC        432
Asn Cys Thr Asp Ala Asn Leu Asn Gly Thr Asn Val Thr Ser Ser Ser
        130                 135                 140
```

```
GGG GGA ACA ATG ATG GAG AAC GGA GAA ATA AAA AAC TGC TCT TTC CAA       480
Gly Gly Thr Met Met Glu Asn Gly Glu Ile Lys Asn Cys Ser Phe Gln
145                 150                 155                 160

GTT ACC ACA AGT AGA AGA GAT AAG ACG CAG AAA AAA TAT GCA CTT TTT       528
Val Thr Thr Ser Arg Arg Asp Lys Thr Gln Lys Lys Tyr Ala Leu Phe
                165                 170                 175

TAT AAA CTT GAT GTG GTA CCA ATA GAG AAG GGT AAT ATT AGC CCT AAG       576
Tyr Lys Leu Asp Val Val Pro Ile Glu Lys Gly Asn Ile Ser Pro Lys
            180                 185                 190

AAT AAT ACT AGC AAT AAT ACT AGC TAT GGT AAC TAT ACA TTG ATA CAT       624
Asn Asn Thr Ser Asn Asn Thr Ser Tyr Gly Asn Tyr Thr Leu Ile His
        195                 200                 205

TGT AAT TCC TCA GTC ATT ACA CAG GCC TGT CCA AAG GTA TCC TTT GAG       672
Cys Asn Ser Ser Val Ile Thr Gln Ala Cys Pro Lys Val Ser Phe Glu
    210                 215                 220

CCA ATT CCC ATA CAT TAT TGC ACC CCG GCT GGT TTT GCG ATT CTA AAG       720
Pro Ile Pro Ile His Tyr Cys Thr Pro Ala Gly Phe Ala Ile Leu Lys
225                 230                 235                 240

TGT AAT GAT AAG AAG TTC AAT GGA ACA GGA CCA TGT AAA AAT GTC AGC       768
Cys Asn Asp Lys Lys Phe Asn Gly Thr Gly Pro Cys Lys Asn Val Ser
                245                 250                 255

ACA GTA CAA TGT ACA CAT GGA ATT AGG CCA GTA GTG TCA ACT CAA CTG       816
Thr Val Gln Cys Thr His Gly Ile Arg Pro Val Val Ser Thr Gln Leu
            260                 265                 270

CTG TTA AAT GGC AGT CTA GCA GAA GAA GAG GTA GTA ATT AGA TCT GAA       864
Leu Leu Asn Gly Ser Leu Ala Glu Glu Glu Val Val Ile Arg Ser Glu
        275                 280                 285

AAT TTC ACG GAC AAT GTT AAA ACC ATA ATA GTA CAG CTG AAT GCA TCT       912
Asn Phe Thr Asp Asn Val Lys Thr Ile Ile Val Gln Leu Asn Ala Ser
    290                 295                 300

GTA CAA ATT AAT TGT ACA AGA CCC AAC AAC AAT ACA AGA AAA AGT ATA       960
Val Gln Ile Asn Cys Thr Arg Pro Asn Asn Asn Thr Arg Lys Ser Ile
305                 310                 315                 320

ACT AAG GGA CCA GGG AGA GTA ATT TAT GCA ACA GGA CAA ATA ATA GGA      1008
Thr Lys Gly Pro Gly Arg Val Ile Tyr Ala Thr Gly Gln Ile Ile Gly
                325                 330                 335

GAT ATA AGA AAA GCA CAT TGT AAC CTT AGT AGA GCA CAA TGG AAT AAC      1056
Asp Ile Arg Lys Ala His Cys Asn Leu Ser Arg Ala Gln Trp Asn Asn
            340                 345                 350

ACT TTA AAA CAG GTA GTT ACA AAA TTA AGA GAA CAA TTT GAC AAT AAA      1104
Thr Leu Lys Gln Val Val Thr Lys Leu Arg Glu Gln Phe Asp Asn Lys
        355                 360                 365

ACA ATA GTC TTT ACG TCA TCC TCA GGA GGG GAC CCA GAA ATT GTA CTT      1152
Thr Ile Val Phe Thr Ser Ser Ser Gly Gly Asp Pro Glu Ile Val Leu
    370                 375                 380

CAC AGT TTT AAT TGT GGA GGG GAA TTT TTC TAC TGT AAT ACA ACA CAA      1200
His Ser Phe Asn Cys Gly Gly Glu Phe Phe Tyr Cys Asn Thr Thr Gln
385                 390                 395                 400

CTG TTT AAT AGT ACT TGG AAT AGT ACT GAA GGG TCA AAT AAC ACT GGA      1248
Leu Phe Asn Ser Thr Trp Asn Ser Thr Glu Gly Ser Asn Asn Thr Gly
                405                 410                 415

GGA AAT GAC ACA ATC ACA CTC CCA TGC AGA ATA AAA CAA ATT GTA AAC      1296
Gly Asn Asp Thr Ile Thr Leu Pro Cys Arg Ile Lys Gln Ile Val Asn
            420                 425                 430

ATG TGG CAG GAA GTA GGA AAA GCA ATG TAT GCC CCT CCC ATC AGT GGA      1344
Met Trp Gln Glu Val Gly Lys Ala Met Tyr Ala Pro Pro Ile Ser Gly
        435                 440                 445

CAA ATT AAA TGT ATA TCA AAT ATT ACA GGG CTA CTA TTA ACA AGA GAT      1392
Gln Ile Lys Cys Ile Ser Asn Ile Thr Gly Leu Leu Leu Thr Arg Asp
```

```
                450                 455                 460
GGG GGT GAA GAT ACA ACT AAT ACT ACA GAG ATC TTC AGA CTT GGA GGA    1440
Gly Gly Glu Asp Thr Thr Asn Thr Thr Glu Ile Phe Arg Leu Gly Gly
465                     470                 475                 480

GGA AAT ATG AGG GAC AAT TGG AGA AGT GAA TTA TAT AAA TAT AAA GTG    1488
Gly Asn Met Arg Asp Asn Trp Arg Ser Glu Leu Tyr Lys Tyr Lys Val
                    485                 490                 495

GTA AGA ATT GAG CCA TTA GGA GTG GCA CCC ACT AGG GCA AAG AGA AGA    1536
Val Arg Ile Glu Pro Leu Gly Val Ala Pro Thr Arg Ala Lys Arg Arg
                500                 505                 510

GTG GTG CAA AGA GAA AAA AGA                                        1557
Val Val Gln Arg Glu Lys Arg
            515

(2) INFORMATION FOR SEQ ID NO:26:

(i) SEQUENCE CHARACTERISTICS:
        (A) LENGTH: 1527 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1527

(xi) SEQUENCE DESCRIPTION: SEQ ID NO:26:

ATG AAA GTG AAG GGG ACC AGG AGG AAT TAT CAG CAC TTG TGG AGA TGG    48
Met Lys Val Lys Gly Thr Arg Arg Asn Tyr Gln His Leu Trp Arg Trp
1               5                   10                  15

GGC ACC TTG CTC CTT GGG ATG TTG ATG ATC TGT AGT GCT ACA GAA AAA    96
Gly Thr Leu Leu Leu Gly Met Leu Met Ile Cys Ser Ala Thr Glu Lys
                20                  25                  30

TTG TGG GTC ACA GTT TAT TAT GGA GTA CCT GTG TGG AAA GAA GCA ACT    144
Leu Trp Val Thr Val Tyr Tyr Gly Val Pro Val Trp Lys Glu Ala Thr
            35                  40                  45

ACC ACT CTA TTT TGT GCA TCA GAT GCT AGA GCA TAT GAT ACA GAG GTA    192
Thr Thr Leu Phe Cys Ala Ser Asp Ala Arg Ala Tyr Asp Thr Glu Val
        50                  55                  60

CAT AAT GTT TGG GCC ACA CAT GCC TGT GTA CCC ACA GAC CCC AAC CCA    240
His Asn Val Trp Ala Thr His Ala Cys Val Pro Thr Asp Pro Asn Pro
65                  70                  75                  80

CAA GAA GTA GTA TTG GGA AAT GTG ACA GAA AAT TTT AAC ATG TGG AAA    288
Gln Glu Val Val Leu Gly Asn Val Thr Glu Asn Phe Asn Met Trp Lys
                85                  90                  95

AAT AAC ATG GTA GAA CAG ATG CAG GAG GAT ATA ATC AGT TTA TGG GAT    336
Asn Asn Met Val Glu Gln Met Gln Glu Asp Ile Ile Ser Leu Trp Asp
                100                 105                 110

CAA AGC CTA AAG CCA TGT GTA AAA TTA ACC CCA CTC TGT GTT ACT TTA    384
Gln Ser Leu Lys Pro Cys Val Lys Leu Thr Pro Leu Cys Val Thr Leu
            115                 120                 125

AAT TGC ACT GAT TTG GGG AAG GCT ACT AAT ACC AAT AGT AGT AAT TGG    432
Asn Cys Thr Asp Leu Gly Lys Ala Thr Asn Thr Asn Ser Ser Asn Trp
        130                 135                 140

AAA GAA GAA ATA AAA GGA GAA ATA AAA AAC TGC TCT TTC AAT ATC ACC    480
Lys Glu Glu Ile Lys Gly Glu Ile Lys Asn Cys Ser Phe Asn Ile Thr
145                 150                 155                 160

ACA AGC ATA AGA GAT AAG ATT CAG AAA GAA AAT GCA CTT TTT CGT AAC    528
Thr Ser Ile Arg Asp Lys Ile Gln Lys Glu Asn Ala Leu Phe Arg Asn
                165                 170                 175
```

```
                                                  -continued

CTT GAT GTA GTA CCA ATA GAT AAT GCT AGT ACT ACT ACC AAC TAT ACC     576
Leu Asp Val Val Pro Ile Asp Asn Ala Ser Thr Thr Thr Asn Tyr Thr
        180                     185                 190

AAC TAT AGG TTG ATA CAT TGT AAC AGA TCA GTC ATT ACA CAG GCC TGT     624
Asn Tyr Arg Leu Ile His Cys Asn Arg Ser Val Ile Thr Gln Ala Cys
        195                     200                 205

CCA AAG GTA TCA TTT GAG CCA ATT CCC ATA CAT TAT TGT ACC CCG GCT     672
Pro Lys Val Ser Phe Glu Pro Ile Pro Ile His Tyr Cys Thr Pro Ala
    210                     215                 220

GGT TTT GCG ATT CTA AAG TGT AAT AAT AAA ACG TTC AAT GGA AAA GGA     720
Gly Phe Ala Ile Leu Lys Cys Asn Asn Lys Thr Phe Asn Gly Lys Gly
225                     230                 235                 240

CCA TGT ACA AAT GTC AGC ACA GTA CAA TGT ACA CAT GGA ATT AGG CCA     768
Pro Cys Thr Asn Val Ser Thr Val Gln Cys Thr His Gly Ile Arg Pro
        245                     250                 255

ATA GTG TCA ACT CAA CTG CTG TTA AAT GGC AGT CTA GCA GAA GAA GAG     816
Ile Val Ser Thr Gln Leu Leu Leu Asn Gly Ser Leu Ala Glu Glu Glu
            260                     265                 270

GTA GTA ATT AGA TCT GAC AAT TTC ACG AAC AAT GCT AAA ACC ATA ATA     864
Val Val Ile Arg Ser Asp Asn Phe Thr Asn Asn Ala Lys Thr Ile Ile
                275                     280                 285

GTA CAG CTG AAT GAA TCT GTA GCA ATT AAC TGT ACA AGA CCC AAC AAC     912
Val Gln Leu Asn Glu Ser Val Ala Ile Asn Cys Thr Arg Pro Asn Asn
    290                     295                 300

AAT ACA AGA AAA AGT ATC TAT ATA GGA CCA GGG AGA GCA TTT CAT ACA     960
Asn Thr Arg Lys Ser Ile Tyr Ile Gly Pro Gly Arg Ala Phe His Thr
305                     310                 315                 320

ACA GGA AGA ATA ATA GGA GAT ATA AGA AAA GCA CAT TGT AAC ATT AGT    1008
Thr Gly Arg Ile Ile Gly Asp Ile Arg Lys Ala His Cys Asn Ile Ser
            325                     330                 335

AGA GCA CAA TGG AAT AAC ACT TTA GAA CAG ATA GTT AAA AAA TTA AGA    1056
Arg Ala Gln Trp Asn Asn Thr Leu Glu Gln Ile Val Lys Lys Leu Arg
                340                     345                 350

GAA CAG TTT GGG AAT AAT AAA ACA ATA GTC TTT AAT CAA TCC TCA GGA    1104
Glu Gln Phe Gly Asn Asn Lys Thr Ile Val Phe Asn Gln Ser Ser Gly
    355                     360                 365

GGG GAC CCA GAA ATT GTA ATG CAC AGT TTT AAT TGT AGA GGG GAA TTT    1152
Gly Asp Pro Glu Ile Val Met His Ser Phe Asn Cys Arg Gly Glu Phe
370                     375                 380

TTC TAC TGT AAT ACA ACA CAA CTG TTT AAT AAT ACA TGG AGG TTA AAT    1200
Phe Tyr Cys Asn Thr Thr Gln Leu Phe Asn Asn Thr Trp Arg Leu Asn
385                     390                 395                 400

CAC ACT GAA GGA ACT AAA GGA AAT GAC ACA ATC ATA CTC CCA TGT AGA    1248
His Thr Glu Gly Thr Lys Gly Asn Asp Thr Ile Ile Leu Pro Cys Arg
                405                     410                 415

ATA AAA CAA ATT ATA AAC ATG TGG CAG GAA GTA GGA AAA GCA ATG TAT    1296
Ile Lys Gln Ile Ile Asn Met Trp Gln Glu Val Gly Lys Ala Met Tyr
                420                     425                 430

GCC CCT CCC ATT GGA GGA CAA ATT AGT TGT TCA TCA AAT ATT ACA GGG    1344
Ala Pro Pro Ile Gly Gly Gln Ile Ser Cys Ser Ser Asn Ile Thr Gly
        435                     440                 445

CTG CTA TTA ACA AGA GAT GGT GGT ACA AAT GTA ACT AAT GAC ACC GAG    1392
Leu Leu Leu Thr Arg Asp Gly Gly Thr Asn Val Thr Asn Asp Thr Glu
    450                     455                 460

GTC TTC AGA CCT GGA GGA GGA GAT ATG AGG GAC AAT TGG AGA AGT GAA    1440
Val Phe Arg Pro Gly Gly Gly Asp Met Arg Asp Asn Trp Arg Ser Glu
465                     470                 475                 480

TTA TAT AAA TAT AAA GTA ATA AAA ATT GAA CCA TTA GGA ATA GCA CCC    1488
Leu Tyr Lys Tyr Lys Val Ile Lys Ile Glu Pro Leu Gly Ile Ala Pro
                485                     490                 495
```

-continued

| | | | | | | | | | | | | |
|---|---|---|---|---|---|---|---|---|---|---|---|---|
| ACC | AAG | GCA | AAG | AGA | AGA | GTG | GTG | CAG | AGA | GAA | AAA | AGA |
| Thr | Lys | Ala | Lys | Arg | Arg | Val | Val | Gln | Arg | Glu | Lys | Arg |
| | | | | 500 | | | | | 505 | | | |

1527